(12) United States Patent
Ronsheim et al.

(10) Patent No.: US 9,284,314 B2
(45) Date of Patent: Mar. 15, 2016

(54) PROCESSES FOR PREPARING HETEROCYCLIC COMPOUNDS INCLUDING TRANS-7-OXO-6-(SULPHOOXY)-1,6-DIAZABICYCLO[3,2,1]OCTANE-2-CARBOXAMIDE AND SALTS THEREOF

(71) Applicants: Melanie Simone Ronsheim, Port Jefferson, NY (US); Saibaba Racha, Smithtown, NY (US); Graham Richard Lawton, Smithtown, NY (US); Shao Hong Zhou, Commack, NY (US); Yuriy B. Kalyan, Staten Island, NY (US); Michael Golden, Macclesfield (GB); David Milne, Macclesfield (GB); Alexander Telford, Macclesfield (GB); Janette Cherryman, Macclesfield (GB); Alistair Boyd, Cheshire (GB); Andrew Phillips, Macclesfield (GB); Mahendra G. Dedhiya, Pomona, NY (US)

(72) Inventors: Melanie Simone Ronsheim, Port Jefferson, NY (US); Saibaba Racha, Smithtown, NY (US); Graham Richard Lawton, Smithtown, NY (US); Shao Hong Zhou, Commack, NY (US); Yuriy B. Kalyan, Staten Island, NY (US); Michael Golden, Macclesfield (GB); David Milne, Macclesfield (GB); Alexander Telford, Macclesfield (GB); Janette Cherryman, Macclesfield (GB); Alistair Boyd, Cheshire (GB); Andrew Phillips, Macclesfield (GB); Mahendra G. Dedhiya, Pomona, NY (US)

(73) Assignee: Forest Laboratories Holdings Ltd., Hamilton (BM)

( * ) Notice: Subject to any disclaimer, the term of this patent is extended or adjusted under 35 U.S.C. 154(b) by 0 days.

(21) Appl. No.: 14/589,194

(22) Filed: Jan. 5, 2015

(65) Prior Publication Data

US 2015/0112070 A1 Apr. 23, 2015

Related U.S. Application Data

(63) Continuation of application No. 14/180,656, filed on Feb. 14, 2014, now Pat. No. 8,969,566, which is a continuation of application No. 13/524,007, filed on Jun. 15, 2012, now Pat. No. 8,829,191.

(60) Provisional application No. 61/498,522, filed on Jun. 17, 2011.

(51) Int. Cl.
| | |
|---|---|
| *C07D 401/04* | (2006.01) |
| *C07D 471/08* | (2006.01) |
| *C07D 211/60* | (2006.01) |
| *C07D 211/56* | (2006.01) |

(52) U.S. Cl.
CPC ............ *C07D 471/08* (2013.01); *C07D 211/56* (2013.01); *C07D 211/60* (2013.01)

(58) Field of Classification Search
CPC ..................................................... C07D 401/04
USPC ......................................................... 546/121
See application file for complete search history.

(56) References Cited

U.S. PATENT DOCUMENTS 7,612,087 B2 * 11/2009 Aszodi et al. ........ A61K 31/439
                                                            514/203

* cited by examiner

*Primary Examiner* — Niloofar Rahmani
(74) *Attorney, Agent, or Firm* — Andrew C. Chien

(57) ABSTRACT

The present invention relates to compounds and processes for preparing compounds of Formula (I),

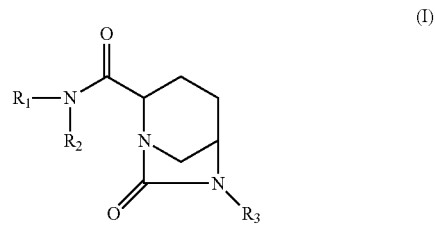

including compounds such as trans-7-oxo-6-(sulphooxy)-1,6-diazabicyclo[3,2,1]octane-2-carboxamide and salts thereof (e.g., NXL-104).

15 Claims, No Drawings

PROCESSES FOR PREPARING HETEROCYCLIC COMPOUNDS INCLUDING TRANS-7-OXO-6-(SULPHOOXY)-1,6-DIAZABICYCLO[3,2,1]OCTANE-2-CARBOXAMIDE AND SALTS THEREOF

CROSS-REFERENCE TO RELATED APPLICATIONS

This application claims priority under 35 U.S.C. §119, based on U.S. Provisional Application Ser. No. 61/498,522 filed on Jun. 17, 2011, which is hereby incorporated by reference in its entirety.

FIELD OF THE INVENTION

The present invention relates to novel compounds and processes for preparing compounds of Formula (I), including compounds such as trans-7-oxo-6-(sulphooxy)-1,6-diazabicyclo[3,2,1]octane-2-carboxamide and salts thereof (e.g., NXL-104).

BACKGROUND OF THE INVENTION

U.S. Pat. No. 7,112,592 discloses novel heterocyclic compounds and their salts, processes for making the compounds and methods of using the compounds as antibacterial agents. One such compound is sodium salt of trans-7-oxo-6-(sulphooxy)-1,6-diazabicyclo[3,2,1]octane-2-carboxamide. PCT Application WO 2002/10172 describes the production of azabicyclic compounds and salts thereof with acids and bases, and in particular, trans-7-oxo-6-sulphoxy-1,6-diazabicyclo[3.2.1]octane-2-carboxamide and its pyridinium, tetrabutylammonium and sodium salts. PCT Application WO 2003/063864 and U.S. Patent Publication No. 2005/0020572 describe the use of compounds including trans-7-oxo-6-(sulphooxy)-1,6-diazabicyclo[3,2,1]octane-2-carboxamide sodium salt, as β-lactamase inhibitors that can be administered alone or in combination with β-lactamine antibacterial agents. U.S. Patent Publication No. 2010/0197928 discloses methods for preparing 2,5-disubstituted piperidine and novel intermediates. PCT Application WO 2011/042560 and U.S. patent application Ser. No. 12/900,567 disclose crystalline forms of trans-7-oxo-6-(sulphooxy)-1,6-diazabicyclo[3,2,1]octane-2-carboxamide sodium salt. These references are incorporated herein by reference, in their entirety.

There is an existing and continual need in the art for new and improved methods for preparing compounds of Formula (I) including trans-7-oxo-6-(sulphooxy)-1,6-diazabicyclo[3,2,1]octane-2-carboxamide, related compounds and salts thereof (e.g., NXL-104). The present invention provides novel compounds and processes for preparing compounds of Formula (I) including trans-7-oxo-6-(sulphooxy)-1,6-diazabicyclo[3,2,1]octane-2-carboxamide, related compounds and salts thereof (e.g., NXL-104).

SUMMARY OF THE INVENTION

According to some embodiments, the present invention provides processes for preparing compounds of Formula (I):

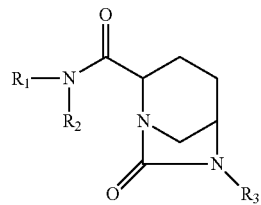

and pharmaceutically acceptable salts, solvates, hydrates, enantiomers or diastereomers thereof (e.g., NXL-104) using compounds of Formula (II).

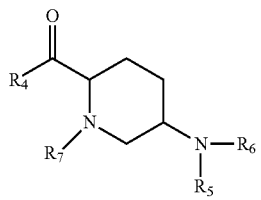

According to some embodiments, the present invention provides compounds of Formula (III) and salts, solvates, hydrates, enantiomers or diastereomers thereof (e.g., (2S, 5R)-5-[(benzyloxy)amino]piperidine-2-carboxamide).

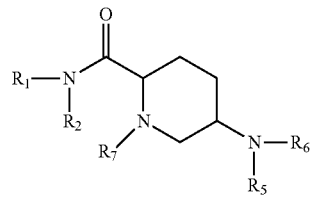

According to some embodiments, the present invention provides compounds of Formula (VI) or salts or analogs thereof

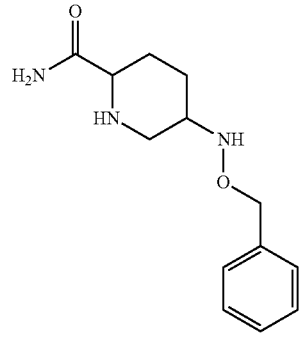

According to some embodiments, the present invention provides processes for preparing a compound of Formula (IX).

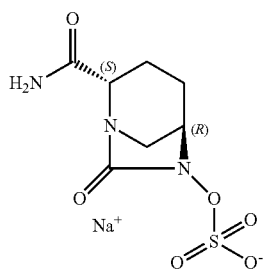

(IX)

According to some embodiments, the present invention provides processes compounds of Formula (XIV) or salts or analogs thereof.

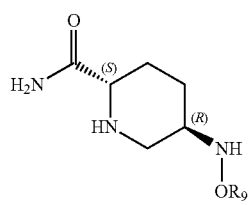

(XIV)

DETAILED DESCRIPTION OF THE INVENTION

The present invention provides novel compounds and improved methods for preparing compounds of Formula (I) and pharmaceutically acceptable salts, solvates, hydrates, enantiomers or diastereomers thereof (e.g., NXL-104).

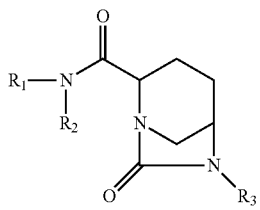

(I)

In some embodiments, the processes comprise treating a compound of Formula (II) with a source of nitrogen or an amine to prepare a compound of Formula (III) and treating the compound of Formula (III) with a protecting group and a carbonylation agent. In further embodiments, the treatment is followed by deprotection.

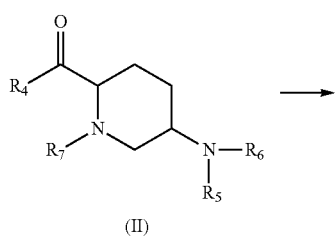

(II)

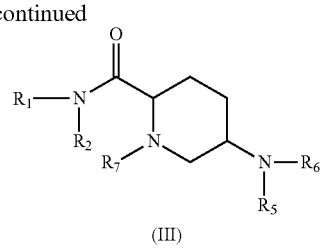

(III)

In some embodiments, R1, R2, R3, R4, R5, R6 and R7 include, but are not limited to, hydrogen, oxygen, nitrogen, amino, carbonyl, carbamoyl, alkyl, alkenyl, alkynyl, alkoxy, cycloalkyl, aryl, aralkyl, trialkylsilyl and heterocycle groups. In specific embodiments, R1, R2, R3, R4, R5, R6 and R7 may be optionally substituted by one or more halogen, oxygen, hydroxy, cyano, nitro, amino, alkylamino, dialkylamino, arylamino, diarylamino, amido, alkylamido, carbamoyl, ureido, dimethylamino, carboxyl, alkyl, allyl, halogenated alkyl, trialkylsilyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkythio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl or a combination thereof.

In other embodiments, R1 and R2 may together form a heterocycle. The heterocycyle may be optionally substituted by one or more halogen, hydroxy, cyano, nitro, amino, alkylamino, dialkylamino, arylamino, diarylamino, amido, alkylamido, carbamoyl, ureido, dimethylamino, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkythio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl or a combination thereof.

In still other embodiments, each of R3, R5 and R6 include COH, COB', COOB', CONH$_2$, CONHB', CONHOH, CONHSO$_2$B', CH$_2$COOH, CH$_2$COOB', CH$_2$CONHOH, CH$_2$CONHCN, CH$_2$tetrazole, protected CH$_2$tetrazole, CH$_2$SO$_3$H, CH$_2$SO$_2$B', CH$_2$PO(OB')$_2$, CH$_2$PO(OB')(OH), CH$_2$PO(B')(OH) and CH$_2$PO(OH)$_2$. B' includes an alkyl containing 1 to 6 carbon atoms optionally substituted by a pyridyl or carbamoyl radical, —CH$_2$-alkenyl containing 3 to 9 carbon atoms, aryl containing 6 to 10 carbon atoms and aralkyl containing 7 to 11 carbon atoms, wherein the nucleus of said aryl or aralkyl is optionally substituted by OH, NH$_2$, NO$_2$, alkyl containing 1 to 6 carbon atoms, alkoxy containing 1 to 6 carbon atoms or by one or more halogen atoms.

In exemplary embodiments, R3, R5 or R6 may be OR' or OP'.

R' includes SO$_3$, SO$_2$, SO$_2$NHCOH, SO$_2$NHCO, SO$_2$NHCOO, SO$_2$NHCONH and SO$_2$NHCONH$_2$. In some embodiments, R' may be substituted by hydrogen or alkyl group optionally substituted by a pyridyl or carbamoyl radical, —CH$_2$-alkenyl containing 3 to 9 carbon atoms, aryl containing 6 to 10 carbon atoms and aralkyl containing 7 to 11 carbon atoms. The nucleus of the aryl or aralkyl may be substituted by OH, NH$_2$, NO$_2$, alkyl containing 1 to 6 carbon atoms, alkoxy containing 1 to 6 carbon atoms or by one or more halogen atoms.

P' includes PO(OH)$_2$, PO$_3$, PO$_2$, PO, PO(OH)(O—), PO$_2$NHCOH, PO$_2$NHCO, PO$_2$NHCOO, PO$_2$NHCONH and PO$_2$NHCONH$_2$. In some embodiments, P' may be substituted by hydrogen or alkyl group optionally substituted by a pyridyl or carbamoyl radical, —CH$_2$-alkenyl containing 3 to 9 carbon atoms, aryl containing 6 to 10 carbon atoms and aralkyl containing 7 to 11 carbon atoms. The nucleus of the aryl or aralkyl is optionally substituted by OH, NH$_2$, NO$_2$, alkyl containing 1 to 6 carbon atoms, alkoxy containing 1 to 6 carbon atoms or by one or more halogen atoms.

In exemplary embodiments, R1 and R2 are hydrogen. In other embodiments, R1 is piperidinyl and R2 is hydrogen. In some examples, R3 is OSO$_3$H.

In some embodiments, R4 is benzyloxy. In other embodiments, R5 is benzyloxy and R6 is hydrogen. In still other embodiments, R5 is allyl or trialkylsilyl and R6 is hydrogen. In some examples, R7 is H. In other embodiments, R7 is carbonyl, carbamoyl, or alkyl and may be optionally substituted by one or more halogen, oxygen, hydroxy, cyano, nitro, amino, alkylamino, dialkylamino, arylamino, diarylamino, amido, alkylamido, carbamoyl, ureido, dimethylamino, carboxyl, alkyl, allyl, halogenated alkyl, trialkylsilyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkythio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl or a combination thereof. In specific embodiments, R7 is carbamoyl.

In exemplary embodiments, R4 and R5 are benzyloxy. In further embodiments, R6 and R7 are hydrogen.

The protecting group may be, for example, 9-fluorenylmethoxycarbonyl (FMOC) group, tert-butoxycarbonyl (BOC) group, benzyloxycarbonyl (CBZ), ethyl- or methyloxycarbonyl, phenoxycarbonyl, allyloxycarbonyl (ALOC) and equivalent groups known to one skilled in the art with the benefit of this disclosure. In specific embodiments, the protecting group is 9-fluorenylmethoxycarbonyl (FMOC) group. In some embodiments, the carbonylation agent may include a carbonyl with two leaving groups. The leaving groups may be chloride or imidazole, for example, in N,N-carbonyl diimidazole (CDI). In further embodiments, the protecting group is removed resulting in cyclization.

In exemplary embodiments, the compounds formed after treatment of compounds of Formula (III) may further be treated with a SO$_3$ complex.

The compounds of Formula (II) may be prepared using compounds of Formula (IV).

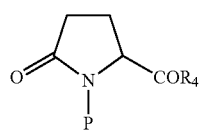

(IV)

R4 is as defined above. In some examples, the compounds of Formula (II) may be prepared according to Scheme I.

Scheme I

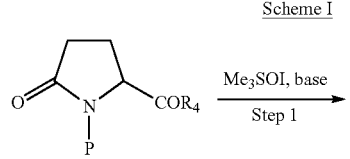

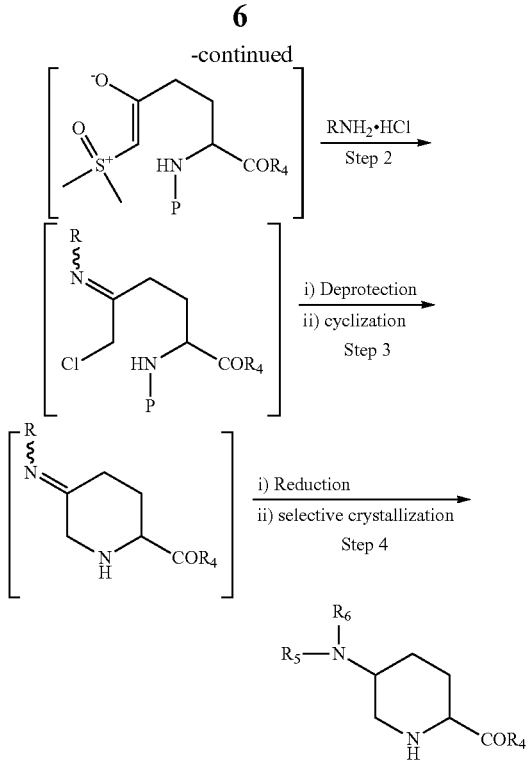

R may be R4, R5 or R6 as defined above. In some embodiments, P may be a protecting group and includes 9-fluorenylmethoxycarbonyl (FMOC), tert-butoxycarbonyl (BOC), benzyloxycarbonyl (CBZ), ethyl- or methyloxycarbonyl, phenoxycarbonyl, allyloxycarbonyl (ALOC) and equivalent groups known to one skilled in the art with the benefit of this disclosure. In exemplary embodiments, P may be tert-butoxycarbonyl (BOC).

In exemplary embodiments, base includes bases capable of deprotonating trimethylsulfoxonium iodide, for example, sodium hydride and potassium tert-butoxide.

In exemplary embodiments, deprotection may include conditions that remove protecting group P; cyclization may include conditions that bring about a 6-exo-tet cyclization to yield a piperidine ring; reduction may include conditions that cause reduction of the oxime bond to a single bond, for example, with an R configuration; selective crystallization may include conditions that allow isolation of the desired isomer, for example, an SR isomer, either as a salt or as the free base. An acid, which may be monovalent or bivalent, may be used to form a solid salt with the desired product.

In some embodiments, a compound of Formula IV is ring-opened with trimethylsulfoxoniumylide and then converted to the α-chloro-oxime in a single step. The protecting group is removed and the compound is cyclized, the oxime is selectively reduced to a hydroxylamine, and a compound of Formula V is isolated, possibly as a salt.

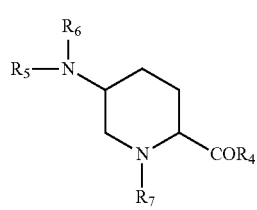

(V)

The compound of Formula (V) may be used to prepare trans-7-oxo-6-(sulphooxy)-1,6-diazabicyclo[3,2,1]octane-2-carboxamide and pharmaceutically acceptable salts thereof (e.g., NXL-104) according to Scheme II below. R4, R5 and R6 are as defined above.

Scheme II

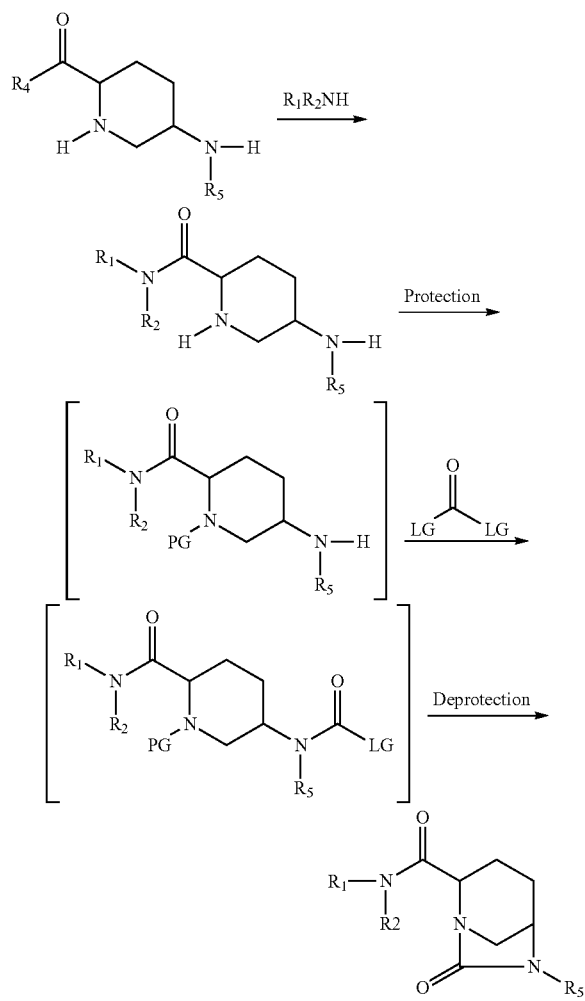

In Scheme II, each of R1 and R2 may be hydrogen or alkyl group.

In exemplary embodiments, the piperidine nitrogen is protected, a phosgenation agent or carbonylation agent is used to install a carbonyl, and the protecting group is removed resulting in cyclization. The hydroxylamine is deprotected, sulfated and converted to a tetraalkylammonium salt.

In some embodiments, the present invention provides compounds of Formula (III) or salts, solvates, hydrates, enantiomers, diastereomers or analogs thereof The R1, R2, R3, R4, R5, R6 and R7 groups are as described above. In some embodiments, R1, R2, R6 and R7 are H and R5 is benzyloxy. For example, the present invention provides compounds of Formula (VI) or salts or analogs thereof.

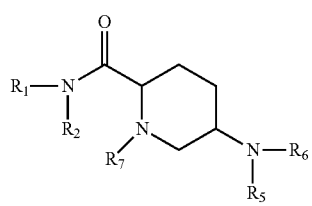

(III)

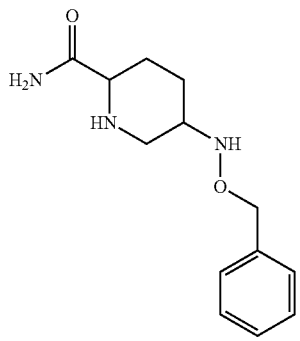

(VI)

In exemplary embodiments, the present invention provides compounds of Formula (VII):

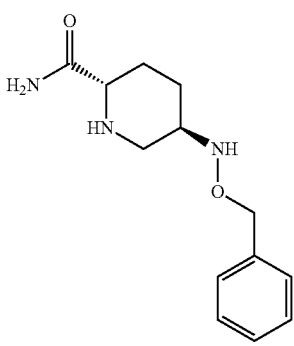

(VII)

R1, R2, R3, R4, R5, R6 and R7 may be any combination of the groups as described above.

In exemplary embodiments, R1, R2 and R6 are hydrogen, R5 is OSO₃H and R7 is carbamoyl. In other examples, R1 is piperidinyl, R2 and R6 are hydrogen, R5 is OSO₃H, and R7 is carbamoyl.

In another aspect, the present invention provides processes for preparing trans-7-oxo-6-(sulphooxy)-1,6-diazabicyclo[3,2,1]octane-2-carboxamide and salts thereof (e.g., NXL-104).

In specific embodiments, the present invention provides methods for making compounds of Formula (VIII) or pharmaceutically acceptable salts thereof (e.g., NXL-104).

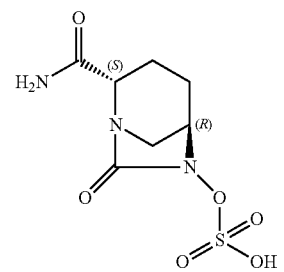

(VIII)

NXL-104 may also be referred to as monosodium salt of (1R,2S,5R)-7-oxo-6-sulphoxy-1,6-diazabicyclo[3.2.1]octane-2-carboxamide, avibactam or sodium ({[(2S,5R)-2-carbamoyl-7-oxo-1,6-diazabicyclo[3.2.1]oct-6-yl]oxy}sulphonyl)oxidanide. The structure of NXL-104 is represented below (Formula IX).

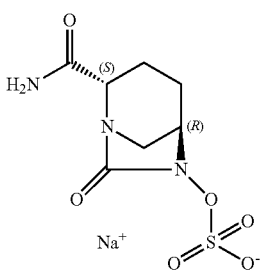

(IX)

In one aspect, the present invention provides methods for making trans-7-oxo-6-(sulphooxy)-1,6-diazabicyclo[3,2,1]octane-2-carboxamide and pharmaceutically acceptable salts thereof (e.g., NXL-104) using compounds according to Scheme III below.

Scheme III

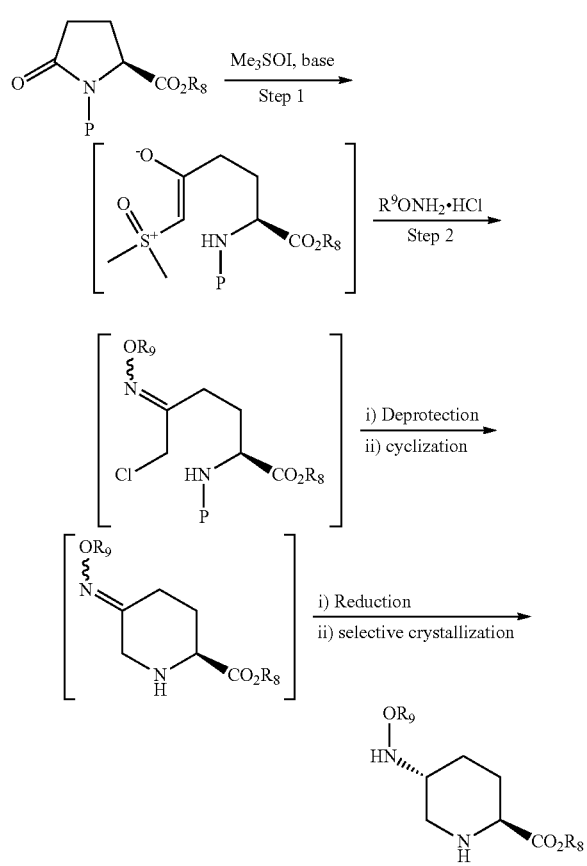

R8 and R9 include any of the groups in any combination as defined for R1 to R7 groups above.

In some embodiments, a compound of Formula (X) is ring-opened with trimethylsulfoxoniumylide and converted to the α-chloro-oxime in a single step.

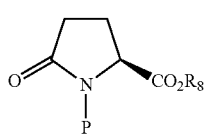

(X)

The protecting group is removed and the compound is cyclized, the oxime is selectively reduced to a hydroxylamine, and a compound of Formula (XI) is isolated, possibly as a salt.

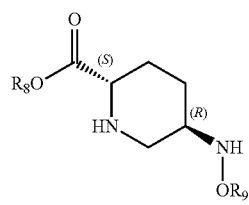

(XI)

In some embodiments, R8 includes alkyl, allyl, aryl, heteroaryl, benzyl, alkoxyalkyl, arylalkoxyalkyl or combinations thereof, and equivalent groups known to one skilled in the art with the benefit of this disclosure. R8 may be a substituted or an unsubstituted alkyl group, which may be linear or branched. For example, R8 may be a methyl, ethyl, propyl, isopropyl, butyl, pentyl or hexyl group. In other embodiments, R8 may be an aryl or an aromatic group. For example, R8 may be a phenyl, naphthyl or furyl group. In exemplary embodiments, R8 may be a benzyl or a substituted benzyl.

In some embodiments, R9 may be a protecting group including alkyl, allyl, acyl, benzyl, H or silyl protecting groups or combinations thereof and equivalent groups known to one skilled in the art with the benefit of this disclosure. For example, R9 may be an allyl, trialkylsilyl or a benzyl group. In exemplary embodiments, R9 may be a benzyl group.

In some embodiments, P may be a protecting group and includes 9-fluorenylmethoxycarbonyl (FMOC), tert-butoxycarbonyl (BOC), benzyloxycarbonyl (CBZ), ethyl- or methyloxycarbonyl, phenoxycarbonyl, allyloxycarbonyl (ALOC) and equivalent groups known to one skilled in the art with the benefit of this disclosure. In exemplary embodiments, P may be tert-butoxycarbonyl (BOC).

In exemplary embodiments, base includes bases capable of deprotonating trimethylsulfoxonium iodide, for example, sodium hydride and potassium tert-butoxide.

In exemplary embodiments, deprotection includes conditions that remove protecting group P; cyclization includes conditions that bring about a 6-exo-tet cyclization to yield a piperidine ring; reduction includes conditions that cause reduction of the oxime bond to a single bond, preferably with an R configuration; selective crystallization includes conditions that allow isolation of the desired isomer, for example, an SR isomer, either as a salt or as the free base. An acid, which may be monovalent or bivalent, may be used to form a solid salt with the desired product.

One skilled in the art will understand with the benefit of this disclosure that that compounds of Formula (X) can be used to prepare compounds of Formula (XI) using conditions and reagents that may yield alternative compounds as intermediates. For example, chlorooxime may be prepared via compounds of Formula (XII) and (XIII) including free base, salts and enantiomers thereof.

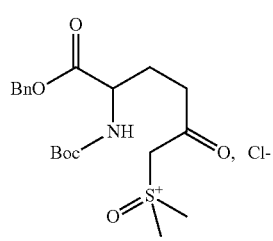

(XII)

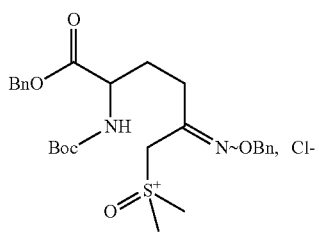

In exemplary embodiments, chloro-oxime may be prepared according to Scheme IV below.

Scheme IV

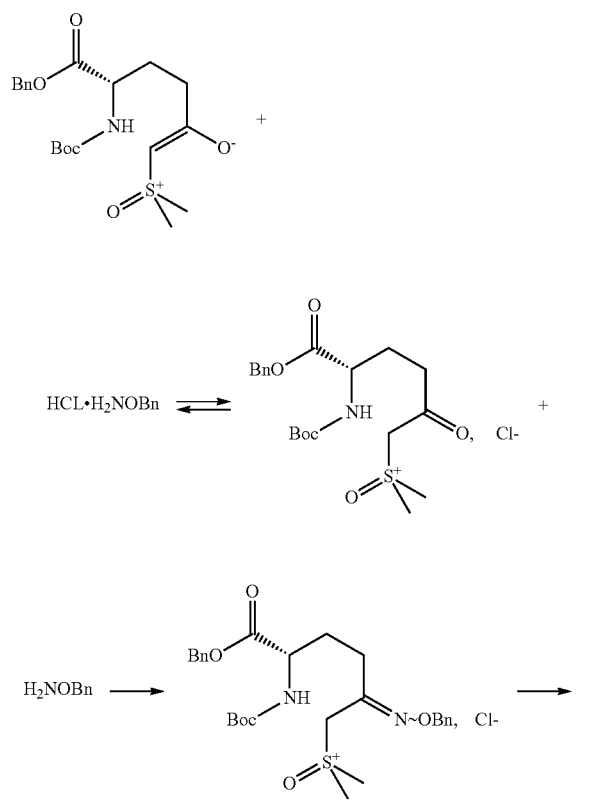

In exemplary embodiments, compounds of Formula (XI) may be used to prepare trans-7-oxo-6-(sulphooxy)-1,6-diazabicyclo[3,2,1]octane-2-carboxamide and pharmaceutically acceptable salts thereof (e.g., NXL-104) according to Scheme V below.

Scheme V

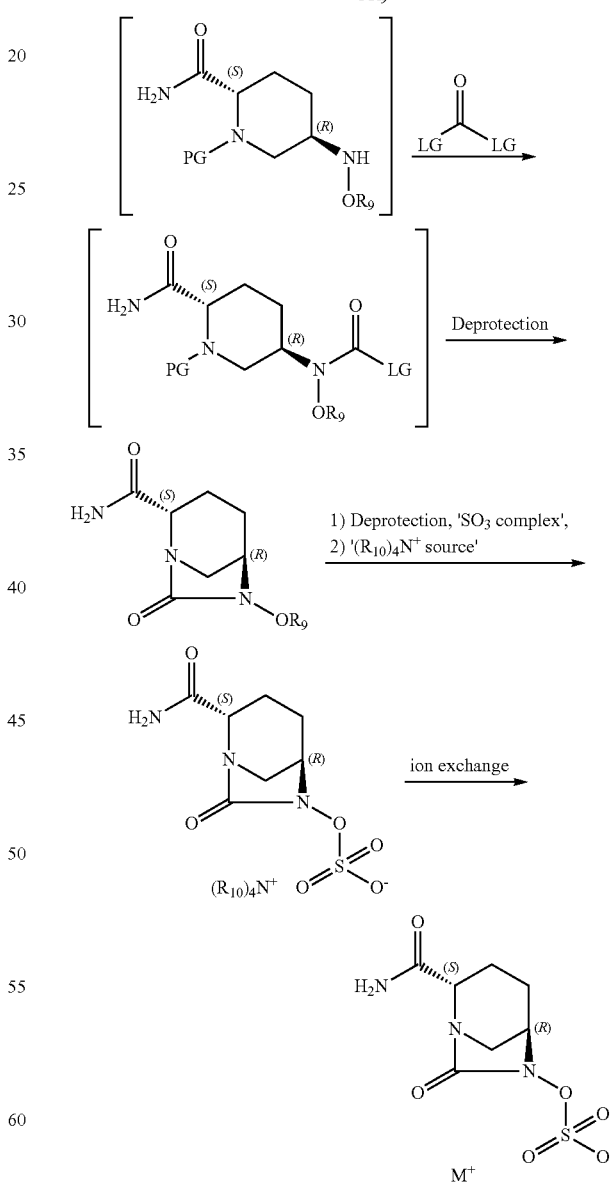

In some embodiments, a compound of Formula (XI) is converted to a compound of Formula (XIV) using an ammonia source.

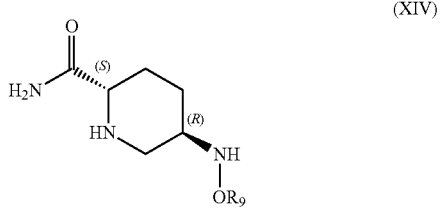

(XIV)

The piperidine nitrogen is protected, a phosgenation or carbonylation agent is used to install a carbonyl, and the protecting group is removed resulting in cyclization. The hydroxylamine is deprotected, sulfated and converted to a tetraalkylammonium salt. The tetraalkylammonium salt is subjected to ion exchange to provide a pharmaceutically acceptable salt of (1R,2S,5R)-7-oxo-6-sulphooxy-1,6-diazabicyclo[3.2.1]octane-2-carboxamide.

In some embodiments, R8 includes alkyl, allyl, aryl, heteroaryl, benzyl, alkoxyalkyl, arylalkoxyalkyl or combinations thereof, and equivalent groups known to one skilled in the art with the benefit of this disclosure. R8 may be a substituted or an unsubstituted alkyl group, which may be linear or branched. For example, R8 may be a methyl, ethyl, propyl, isopropyl, butyl, pentyl or hexyl group. In other embodiments, R8 may be an aryl or an aromatic group. For example, R8 may be a phenyl, naphthyl or furyl group. In exemplary embodiments, R8 may be a benzyl or a substituted benzyl.

In some embodiments, R9 may be a functional group suitable for the protection of hydroxylamines. Examples of suitable R9 groups include alkyl, allyl, acyl, benzyl, H or silyl protecting groups or combinations thereof and equivalent groups known to one skilled in the art with the benefit of this disclosure. In some embodiments, R9 may be an allyl, trialkylsilyl or a benzyl group. In exemplary embodiments, R9 may be a benzyl group.

In exemplary embodiments, NH$_3$ may be ammonia, a source of ammonia, or an ammonia proxy. For example, ammonia proxy may be formamidine and a base. In some embodiments, the ammonia may be dissolved in a polar solvent such as methanol, water, isopropanol and dioxane.

In exemplary embodiments, PG includes a protecting group, LG includes a leaving group; deprotection includes conditions for the removal of the protecting group; SO$_3$ complex includes a sulfur trioxide complex; and (R10)$_4$N$^+$ source includes a tetra n-alkylammonium ion source.

The protecting group may be, for example, 9-fluorenylmethoxycarbonyl (FMOC) group, tert-butoxycarbonyl (BOC) group, benzyloxycarbonyl (CBZ), ethyl- or methyloxycarbonyl, phenoxycarbonyl, allyloxycarbonyl (ALOC) and equivalent groups known to one skilled in the art with the benefit of this disclosure. In specific embodiments, the protecting group is 9-fluorenylmethoxycarbonyl (FMOC) group.

The leaving group may be an imidazole, for example, in N,N-carbonyl diimidazole (CDI).

Deprotection includes conditions for the removal of the protecting group R9, for example, hydrogenation if R9 is benzyl. The SO$_3$ complex may be sulfur trioxide complex such as SO$_3$.pyridine, SO$_3$.dimethylformamide, SO$_3$.triethylamine, SO-$_3$.trimethylamine, chlorosulfonic acid and oleum.

The (R$_{10}$)$_4$N$^+$ source may be a tetra n-alkylammonium ion source, such as tetraethylammonium chloride, tetramethylammonium hydroxide, tetrabutylammonium acetate and tetrabutylammonium bisulphate.

The ion exchange step converts the tetralkylammonium salt to a pharmaceutically acceptable salt, e.g., sodium, potassium, calcium and magnesium. This can be accomplished by crystallization of the salt, e.g., the sodium salt using a source of sodium that may be any salt or form of sodium that allows ion exchange with the tetraalkylammonium. The sodium source may be a sodium carboxylate salt, or an ion exchange resin containing sodium. In exemplary embodiments, the sodium source is sodium 2-ethylhexanoate.

Alternatively, other pharmaceutically acceptable salts of (1R,2S,5R)-7-oxo-6-sulphooxy-1,6-diazabicyclo[3.2.1]octane-2-carboxamide may be prepared in analogous fashion. For example, the potassium salt may be prepared using soluble potassium salts.

In specific embodiments, sodium salt of (1R,2S,5R)-7-oxo-6-sulphooxy-1,6-diazabicyclo[3.2.1]octane-2-carboxamide is prepared using benzyl (2S,5R)-5-[(benzyloxy)amino]piperidine-2-carboxylate ethanedioate (1:1) using Scheme VI.

Scheme VI

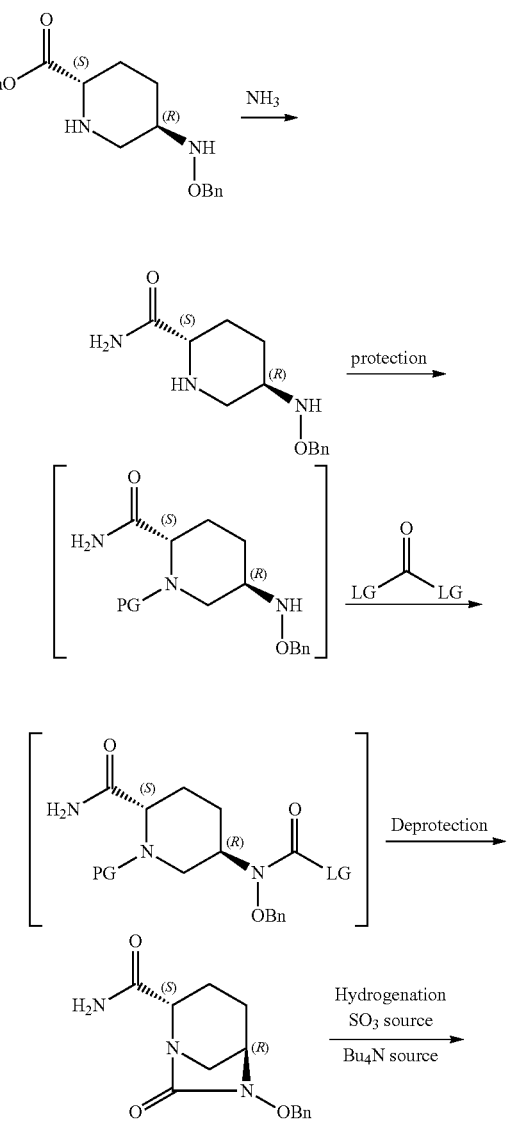

-continued

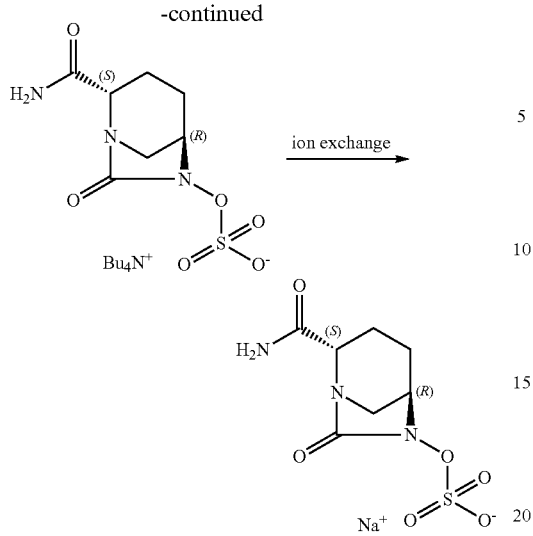

In exemplary embodiments, compounds described herein, for example, benzyl (2S,5R)-5-[(benzyloxy)amino]piperidine-2-carboxylate ethanedioate (1:1) may be treated with ammonia dissolved in a polar solvent such as methanol, water, isopropanol or dioxane. After removal of any by-product, the mixture may be crystallized from a non-polar solvent. Examples of suitable solvents are toluene, cyclopentyl methyl ether (CPME), methyl tert-butyl ether (MTBE), and isohexane. (2S,5R)-5-[(benzyloxy)amino]piperidine-2-carboxamide (amide) may be protected at the piperidine nitrogen with a protecting group prior to the addition of a phosgenation or carbonylation agent, before deprotecting the piperidine nitrogen, cyclizing under basic conditions and isolating the product by crystallization. The protecting group may be FMOC, BOC or CBZ and may be provided in an organic solvent such as toluene, chlorobenzene or fluorobenzene. Examples of suitable phosgenation or carbonylation agents are CDI, phosgene and triphosgene. For the deprotection of an FMOC protecting group, examples of suitable reagents are diethylamine, piperidine, and morpholine. Deprotection of other protecting groups can be accomplished using methods known to those skilled in the art with the benefit of this disclosure. Examples of bases for the cyclization include diethylamine, piperidine, morpholine triethylamine, diisopropylethylamine and aqueous bases such as sodium bicarbonate solution.

(2S,5R)-6-(benzyloxy)-7-oxo-1,6-diazabicyclo[3.2.1]octane-2-carboxamide may further be debenzylated by treatment with hydrogen in the presence of a catalyst (such as palladium, platinum, rhodium, nickel) and in the presence of a base (such as a triethylamine, diisopropylethylamine) and a source of $SO_3$ (such as $SO_3$.pyridine, SO-$_3$.dimethylformamide, $SO_3$.triethylamine, $SO_3$.trimethylamine) and a solvent (such as methanol, ethanol, isopropanol, propanol, butanol, water or mixtures of the same). The product may then be treated with a tetrabutylammonium ion source (such as tetrabutylammonium acetate, tetrabutylammonium bisulphate), extracted into an organic solvent and crystallized from an organic solvent (such as methyl isobutyl ketone (MIBK), acetone, isopropylacetate).

Tetrabutylammonium ({[(2S,5R)-2-carbamoyl-7-oxo-1,6-diazabicyclo[3.2.1]oct-6-yl]oxy}sulphonyl]oxidanide is then dissolved in a solvent (such as ethanol, isopropanol, propanol, water or mixtures of the same) and treated with a sodium carboxylate salt (such a sodium-2-ethylhexanoate).

In another aspect, sodium salt of (1R,2S,5R)-7-oxo-6-sulphooxy-1,6-diazabicyclo[3.2.1]octane-2-carboxamide may be prepared using compounds according to Scheme VII.

Scheme VII

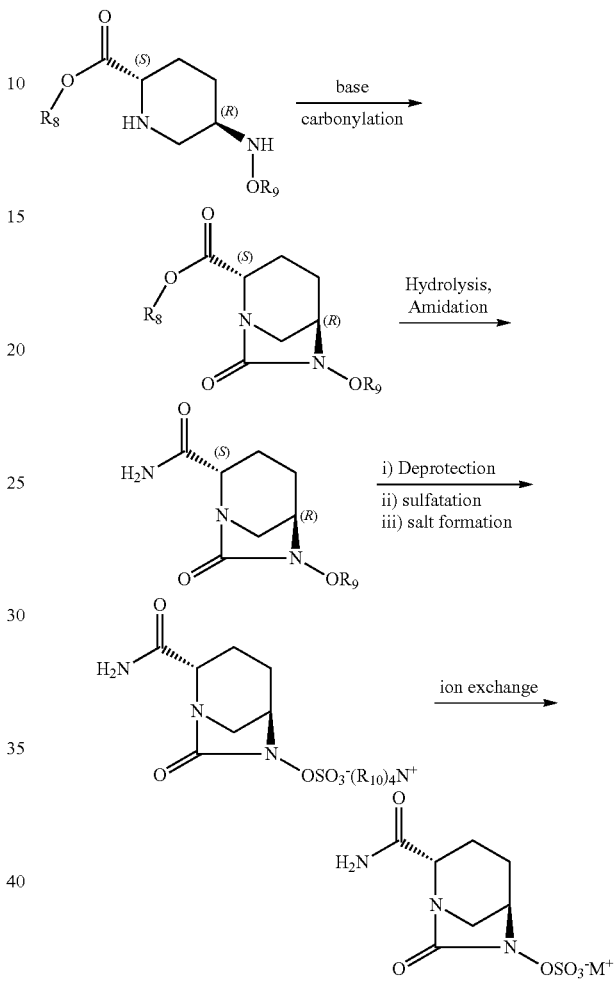

In the presence of base, compound of Formula (XI) reacts with a phosgenation or carbonylation agent to give the cyclic urea. The ester protecting group is removed and the resulting acid is converted to a carboxamide. The hydroxylamine is deprotected, sulfated and converted to a tetraalkylammonium salt. The tetraalkylammonium salt is subjected to ion exchange to provide a pharmaceutically acceptable salt of (1R,2S,5R)-7-oxo-6-sulphooxy-1,6-diazabicyclo[3.2.1]octane-2-carboxamide.

R8 and R9 may represent groups as described above. In specific embodiments, base includes a base for the deprotonation of benzyl (2S,5R)-5-[(benzyloxy)amino]piperidine-2-carboxylate ethanedioate (1:1), for example, an inorganic base, such as $KHCO_3$, or an organic base, such as triethylamine, 3-picoline, pyridine and lutidine; carbonylation includes an addition of a carbonyl group using a single reagent (e.g. triphosgene, N,N-carbonyl diimidazole (CDI), $C(O)(SMe)_2$) or a combination of reagents (e.g provided in the scheme discussed above, or use of $CO_2$ and chlorotrimethylsilane, followed by $SOCl_2$ and pyridine); hydrolysis includes selective cleavage of the CO bond to liberate R7O$^-$, for example, using tetrabutylammonium hydroxide (TBAOH), LiOH, NaOH, iodotrimethylsilane (TMSI). Alternatively, this step can be replaced by other deprotection conditions, for example, when R8=CH$_2$C$_6$H$_5$, hydrogenation, or if R8=allyl, isomerization with Pd; amidation includes the activation of acidic functionality followed by quenching with an ammonia source, either sequentially or concurrently. For example, the acid may be activated using such reagents as alkyl chloroformates, trimethylacetyl chloride, thionyl chloride, diethylchlorophosphate, CDI. The resulting activated acid may be quenched with ammonia or solutions, salts, or sources of ammonia, or with an ammonia proxy such as hexamethyldisilazane (HMDS). Alternatively, the activation and quench may be concurrent using such reagent combinations as diimides, for example, N,N'-dicyclohexylcarbodiimide (DCC) and N-(3-dimethylaminopropyl)-N'-ethylcarbodiimide hydrochloride (EDC) or 1-propanephosphonic acid cyclic anhydride with HMDS; deprotection includes removal of the R9 protecting group to give the free hydroxylamine; sulfatation includes addition of an SO$_3$ group to a hydroxy group using a source of SO$_3$, e.g., SO$_3$.DMF, SO$_3$.NMe$_3$ and ClSO$_3$H; salt formation includes addition of a tetra n-alkylammonium ion source, for example, tetra n-butylammonium acetate, and isolation of the resulting salt.

In some embodiments, deprotection may be achieved using methods known to those skilled in the art with the benefit of this disclosure. For example, hydrogenation using a palladium catalyst may be used if R9 is benzyl.

In another aspect of the invention, (1R,2S,5R)-7-oxo-6-sulphooxy-1,6-diazabicyclo[3.2.1]octane-2-carboxamide may be prepared using a compound of Formula (XV).

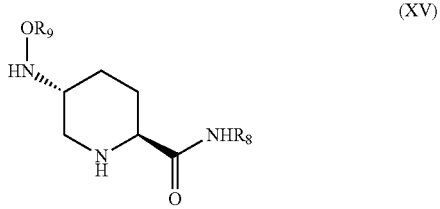

(XV)

These compounds of Formula (XV) may be prepared according to Scheme VIII.

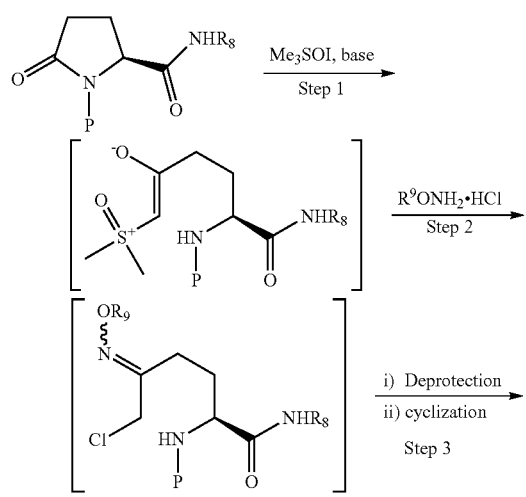

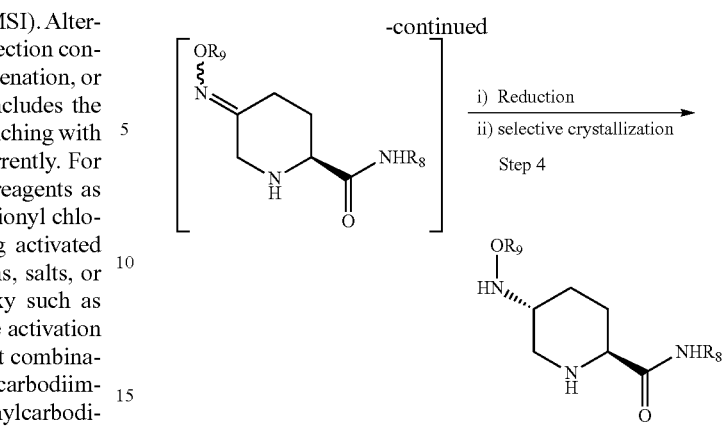

A compound of Formula (XVI) is ring-opened with trimethylsulfoxonium ylide and converted to the α-chloro-oxime.

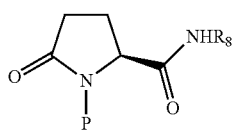

(XVI)

The protecting group is removed and the compound is cyclized, the oxime is selectively reduced to a hydroxylamine, and the final compound is isolated, possibly as a salt. In some embodiments, R8 includes any alkyl, allyl, aryl, benzyl, heterocyclic and equivalent groups for the protection of carboxamides known to one skilled in the art with the benefit of this disclosure. In specific embodiments, R8 may be a tert-butyl, benzyl, allyl, methoxymethyl, silyl, tetrahydropyran or siloxyalkyl group. In exemplary embodiments, R8 may be a benzyl or a substituted benzyl.

In some embodiments, R9 may be a protecting group including alkyl, allyl, acyl, benzyl, H or silyl protecting groups and equivalent groups known to one skilled in the art with the benefit of this disclosure. For example, R9 may be an allyl, trialkylsilyl, or preferably a benzyl group.

In exemplary embodiments, P may be a protecting group, for example, a carbamate protecting group such as tert-butoxycarbonyl (BOC) or benzyloxycarbonyl.

In exemplary embodiments, base in Step 1 includes bases capable of deprotonating trimethylsulfoxonium iodide, for example, sodium hydride and potassium tert-butoxide.

In exemplary embodiments, deprotection includes conditions that remove protecting group P; cyclization includes conditions that bring about a 6-exo-tet cyclization to yield a piperidine ring; reduction includes conditions that cause reduction of the oxime bond to a single bond, preferably with an R configuration; selective crystallization includes conditions that allow isolation of the desired SR isomer, either as a salt or as the free base. An acid, which may be monovalent or bivalent, may be used to form a solid salt with the desired product.

The compounds obtained using the scheme discussed above may be used to prepare sodium salt of (1R,2S,5R)-7-oxo-6-sulphooxy-1,6-diazabicyclo[3.2.1]octane-2-carboxamide according to Scheme IX.

Scheme IX

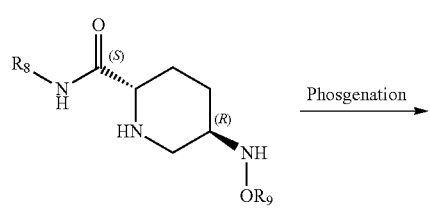

Phosgenation →

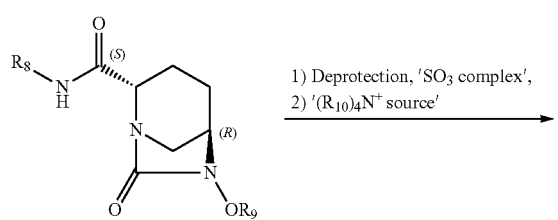

1) Deprotection, 'SO₃ complex',
2) '(R₁₀)₄N⁺ source' →

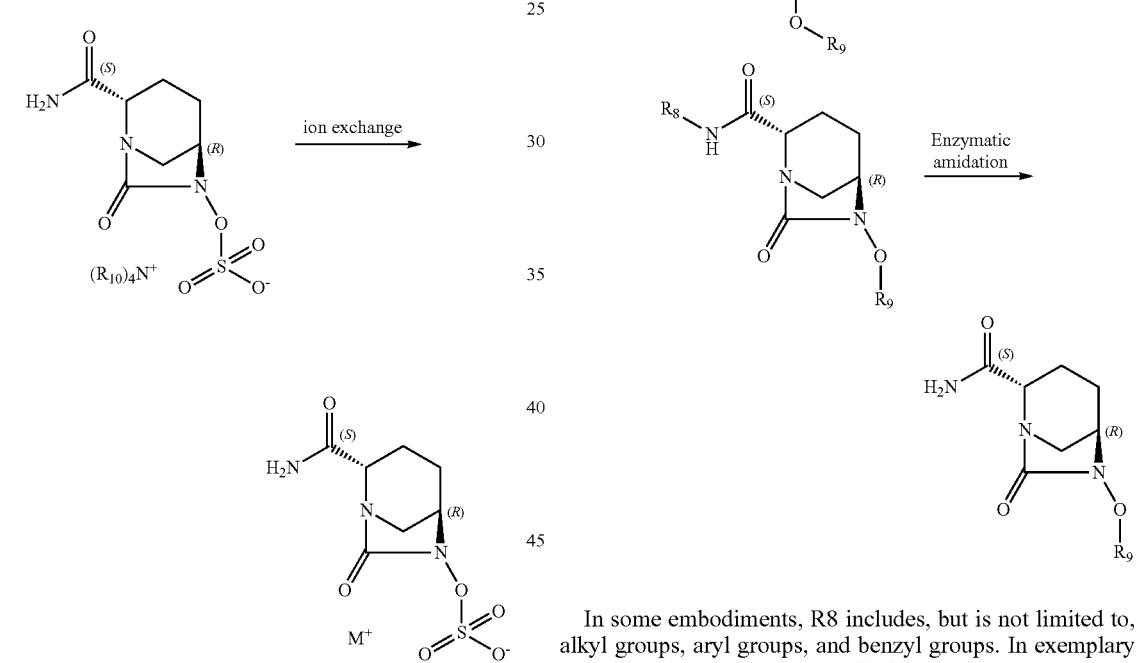

A compound of Formula (XV) is converted to the urea, which is then deprotected, sulfated and converted to the tetraalkylammonium salt. The tetraalkylammonium salt is subjected to ion exchange to provide a pharmaceutically acceptable salt of (1R,2S,5R)-7-oxo-6-sulphooxy-1,6-diazabicyclo[3.2.1]octane-2-carboxamide. R7 and R9 groups are as defined above. Phosgenation or carbonylation is the addition of a carbonyl using either a single reagent, e.g., triphosgene, CDI, or combination of reagents, such as those described in the Schemes above. Deprotection includes the removal of R8 and R9, either concurrently or sequentially. Other steps have been described elsewhere.

In some embodiments, trans-7-oxo-6-(sulphooxy)-1,6-diazabicyclo[3.2.1]octane-2-carboxamide and salts thereof (e.g., NXL-104) may be prepared using enzymes. For example, the processes may involve making a compound of Formula (XVII).

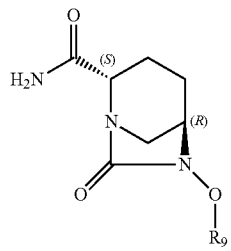

The compound (Formula XVII) may be prepared according to Scheme X.

Scheme X

In some embodiments, R8 includes, but is not limited to, alkyl groups, aryl groups, and benzyl groups. In exemplary embodiments, R8 may be an alkyl group. For example, R8 may be methyl or ethyl.

In some embodiments, R9 may be a functional group suitable for the protection of hydroxylamines. For example, R9 may be an allyl, trialkylsilyl, or a benzyl group.

In exemplary embodiments, phosgenation or carbonylation may be performed with a phosgenating agent, such as triphosgene.

In exemplary embodiments, enzymatic amidation is performed using a enzyme. For example, *Candida antarctica* Lipase A or *Candida antarctica* Lipase B, in the presence of an ammonia source such as ammonium carbamate, ammonia, ammonium chloride or hexamethyldisilazane and a solvent such as acetonitrile, dioxane or chlorobutane.

The processes described herein may be useful for preparing compounds in sufficient purity without isolation. For example, the use of a base (such as potassium tert-butoxide) may yield sufficiently pure beta-keto sulfoxonium (BKS) that could be used in subsequent steps without a need for isolation. In some embodiments, the processes may involve a single step conversion using a single solvent and a single reagent. For example, beta-keto sulfoxonium may be converted to chloroxime in a single solvent with a single reagent. In other embodiments, the processes may use improved reduction conditions that may give a higher ratio of a desired SR isomer to an undesired SS isomer. For example, the ratio may be more than 1. In some embodiments, the ratio of the desired SR isomer to the undesired SS isomer may range from 1 to 10. In exemplary embodiments, the ratio may be 4. In still other embodiments, the processes may provide improved crystallization conditions that may allow selective isolation of desired SR isomer in high purity. In some embodiments, the processes may provide a high yield of pure intermediate compounds, thus, obviating the need to isolate the intermediates. For example, the processes described herein may provide a very high yield of pure benzyl (2S,5R)-5-[(benzyloxy)amino]piperidine-2-carboxylate ethanedioate (1:1). In such cases, isolation of intermediates may not be necessary.

The processes described herein may provide compounds in unexpected high yields and may thus, be efficient and cost-effective.

Unless defined otherwise, all technical and scientific terms used herein generally have the same meaning as commonly understood by one of ordinary skill in the art to which this invention belongs.

"NXL-104" refers to the monosodium salt of (1R,2S,5R)-7-oxo-6-sulphooxy-1,6-diazabicyclo[3.2.1]octane-2-carboxamide or alternatively, sodium ({[(2S,5R)-2-carbamoyl-7-oxo-1,6-diazabicyclo[3.2.1]oct-6-yl]oxy}sulphonyl) oxidanide or avibactam, and is represented by structure shown below.

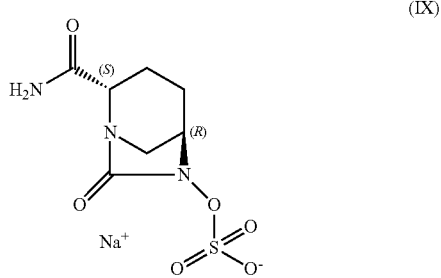

(IX)

As used herein the term "halogen" means F, Cl, Br, and I.

The term "alkyl" means a substituted or unsubstituted saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "halogenated alkyl" means a saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms, that is substituted by one ore more halogens, such as, but not limited to, —$CF_3$, $CF_2CF_3$, $CHF_2$, $CH_2F$, and the like. The use of the term "halogenated alkyl" should not be construed to mean that a "substituted alkyl" group may not be substituted by one or more halogens.

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably, the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "amino" means —$NH_2$.

The term "alkylamino" means —NH(alkyl), wherein alkyl is as described above.

The term "dialkylamino" means —$N(alkyl)_2$, wherein alkyl is as described above.

The term "aryl" means a substituted or unsubstituted aromatic monocyclic or bicyclic ring system comprising about 5 to about 14 carbon atoms, e.g., about 6 to about 10 carbon atoms. Suitable aryl groups include, but are not limited to, phenyl, naphthyl, anthracenyl.

Substituted aryl groups include the above-described aryl groups which are substituted one or more times by, for example, but not limited to, halogen, hydroxyl, amino, carboxy, alkylamino, dialkylamino, aryl, heteroaryl, alkoxy, nitro and cyano, and combinations thereof.

The term "arylamino" means —NH(aryl), wherein aryl is as described above.

The term "diarylamino" means —$N(aryl)_2$, wherein aryl is as described above.

The term "amido" means —$CONH_2$.

The term "arylalkyl" refers to an -(alkylene)-aryl group in which the aryl and alkylene portions are in accordance with the previous descriptions. Suitable examples include, but are not limited to, benzyl, 1-phenethyl, 2-phenethyl, phenpropyl, phenbutyl, phenpentyl, and napthylmethyl.

The term "carboxyl" means —C(O)OH.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "cycloalkylalkyl" means a -(alkylene)-cycloalkyl in which the cycloalkyl group is as previously described; e.g., cyclopropylmethyl, cyclobutylmethyl, cyclopentylethyl, or cyclohexylmethyl, and the like.

The term "heteroaryl" means a substituted or unsubstituted aromatic monocyclic or multicyclic ring system comprising 5 to 14 ring atoms, preferably about 5 to about 10 ring atoms and most preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, benzimidazolyl, indazolyl, indolyl, quinolinyl, isoquinolinyl, naphthyridinyl and the like.

Substituted heteroaryl groups include the above-described heteroaryl groups which are substituted one or more times by, for example, but not limited to, halogen, hydroxyl, amino, carboxy, alkylamino, dialkylamino, aryl, heteroaryl, alkoxy, nitro and and combinations thereof.

The term "heteroarylalkyl" refers to a -(alkylene)-heteroaryl group wherein the heteroaryl and alkylene portions are in accordance with the previous descriptions. Suitable examples include, but are not limited to, pyridylmethyl, thiazolylmethyl, thienylmethyl, pyrimidinylmethyl, pyrazinylmethyl, and isoquinolinylmethyl, and the like.

The term "heterocycle" means a substituted or unsubstituted non-aromatic mono- or multicyclic ring system comprising 3 to 10 atoms, preferably 5 or 6, wherein at least one of the ring atoms is an N, O or S atom. Suitable heterocyle groups include, but are not limited to tetrahydrofuranyl, tetrahydrothienyl, tetrahydropyranyl, dihydropyranyl, pyrrolidinyl, piperidinyl, piperazinyl, thiomorpholinyl, morpholinyl, isoxazolinyl, and the like.

Substituted heterocycle groups include the above-described heterocycle groups which are substituted one or more times by, for example, halogen, amino, alkyl, hydroxy, carboxy, and combinations thereof. Heterocycle groups may also be substituted by, e.g., aryl or heteroaryl.

The term "heterocyclealkyl" refers to a -(alkylene)-heterocycle group wherein the heterocycle and alkylene portions are in accordance with the previous discussions.

The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, cycloalkyl-C(O)—, aryl-C(O)—, or heteroalkyl-C(O)—, in which the various groups are as previously described, e.g., acetyl, propionyl, benzoyl, pyridinylcarbonyl, and the like.

The term "alkoxy" means alkyl-O— groups in which the alkyl portion is in accordance with the previous descriptions. Suitable alkoxy groups include, but are not limited to, methoxy, ethoxy, n-propoxy, iso-propoxy, n-butoxy, t-butoxy, pentoxy, hexoxy, heptoxy, octoxy, and the like. For example, the alkoxy can be methoxy or ethoxy.

The term "aryloxy" means an aryl-O— group, in which the aryl group is as previously described.

The term "heteroaryloxy" means an heteroaryl-O— group, in which the heteroaryl group is as previously described.

The term "cycloalkylalkyloxy" means a —O-(alkylene)-cycloalkyl group, in which the cycloalkyl and alkylene groups are as previously described.

The term "alkylthio" means an alkyl-S— group, in which the alkyl group is as previously described.

The term "arylthio" means an aryl-S— group, in which the aryl group is as previously described.

The term "alkylsulfinyl" means a —SOR radical where R is alkyl as defined above, e.g., methylsulfinyl, ethylsulfinyl, and the like.

The term "alkylsulfonyl" means a —SO$_2$R radical where R is alkyl as defined above, e.g., methylsulfonyl, ethylsulfonyl, and the like.

The term "arylsulfinyl" means a —SOR radical where R is aryl as defined above, e.g., phenylsulfinyl, and the like.

The term "arylsulfonyl" means a —SO$_2$R radical where R is aryl as defined above, e.g., phenylsulfonyl, and the like.

The term "heteroarylsulfinyl" means a —SOR radical where R is heteroaryl as defined above.

The term "heteroarylsulfonyl" means a —SO$_2$R radical where R is heteroaryl as defined above.

The term "alkoxycarbonyl" means an alkyl-O—C(O)— group, in which the alkyl group is as previously described.

The term "aryloxycarbonyl" means an aryl-O—C(O)— group, in which the aryl group is as previously described.

The term "heteroaryloxycarbonyl" means an heteroaryl-O—C(O)— group, in which the heteroaryl group is as previously described.

The term "cycloalkyloxy" means a —O-cycloalkyl group in which the cycloalkyl group is as previously described, e.g., cyclopropyloxy, cyclobutyloxy, cyclopentyloxy, cyclohexyloxy, and the like The term "arylalkyloxy" means —O-(alkylene)-aryl group, in which the aryl and alkylene groups are as previously described.

The term "heteroarylalkyloxy" means —O-(alkylene)-heteroaryl group, in which the heteroaryl and alkylene groups are as previously described.

One of ordinary skill in the art will recognize that compounds of the present invention can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art with the benefit of this disclosure, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of the invention can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2$H, 3H, $^{11}$C, $^{13}$C and/or $^{14}$C. In one particular embodiment, the compounds contain $^2$H. In another embodiment, the compounds contain $^3$H. Deuterated and tritiated compounds may be prepared using methods known in the art.

For example, deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp; Kabalka, George W.; Varma, Rajender S. The synthesis of radiolabeled compounds via organometallic intermediates. Tetrahedron (1989), 45(21), 6601-21; and Evans, E. Anthony. Synthesis of radiolabeled compounds, J. Radioanal. Chem. (1981), 64(1-2), 9-32.

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art with the benefit of this disclosure will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, aDIPEAtes, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of the present invention can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of the present invention can exist in different solvate forms. Solvates of the compounds of the invention may also form when solvent molecules are incorporated into the crystalline lattice structure of the compound molecule during the crystallization process.

The following examples are merely illustrative of the present invention and should not be construed as limiting the scope of the invention in any way as many variations and equivalents that are encompassed by the present invention will become apparent to those skilled in the art upon reading the present disclosure. For example, some reactions described below may be carried out under a range of conditions, such as at a different temperature (4° C., 10° C., 25° C., etc.), substitution with other reagents and different amounts or concentration of reagents.

EXAMPLES

Example 1

Preparation of benzyl (2S,5R)-5-[(benzyloxy)amino] piperidine-2-carboxylate ethanedioate (1:1) and analogs

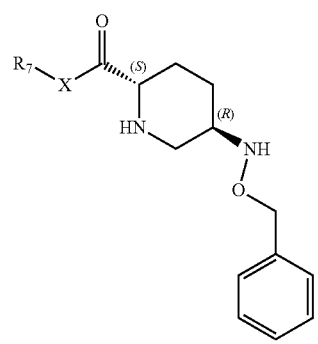

(XVIII)

The compounds of Formula (XVIII) (X=O, NH; R7=benzyl, ethyl) may be prepared as described below.

Example 1a

Benzyl (2S,5R)-5-[(benzyloxy)amino]piperidine-2-carboxylate ethanedioate (1:1) may be prepared as described below.

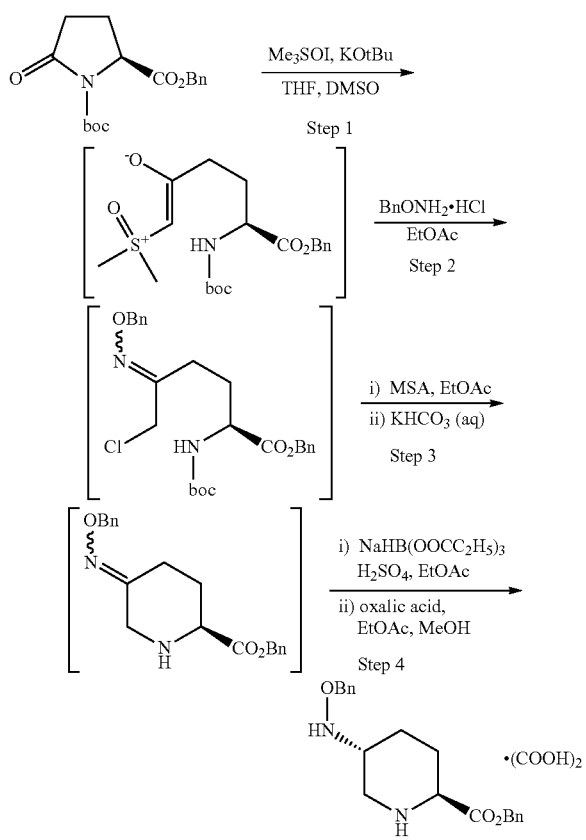

Dimethylsulfoxide (DMSO; 500 ml) was added to a mixture of trimethylsulfoxonium iodide (ME₃SOI; 79.2 g, 360 mmol, 1.15 eq) and potassium tert-butoxide (KOtBu; 38.6 g, 344.4 mmol, 1.1 eq) in tetrahydrofuran (THF; 400 ml) at room temperature. The mixture was stirred until the reaction was deemed to be complete and cooled to −12° C. A solution of (S)-5-oxo-pyrrolidine-1,2-dicarboxylic acid 2-benzyl ester 1-tert-butyl ester (100 g, 313.1 mmol, 1 eq) in tetrahydrofuran (THF; 300 ml) was added slowly. The mixture was stirred at −12° C. until the reaction was deemed to be complete. The reaction was quenched by the addition of saturated aqueous ammonium chloride (500 ml) and water (300 ml). The product was extracted with ethyl acetate (1000 ml), and the resulting organic solution was washed with aqueous sodium chloride. The organic layer was concentrated in vacuo to a final volume of 600 ml.

To this solution was added O-benzylhydroxylamine hydrochloride (BnONH₂HCl; 52.5 g, 328.8 mmol, 1.05 eq) and ethyl acetate (400 ml). The mixture was stirred at reflux until the reaction was deemed to be complete. The mixture was cooled and washed with water and saturated sodium chloride. The organic layer was concentrated in vacuo to afford a solution of (S)-5-Benzyloxyimino-2-tert-butoxycarbonylamino-6-chloro-hexanoic acid benzyl ester in ethyl acetate.

Methane sulfonic acid (MSA; 61 ml, 939.3 mmol, 3 eq) was added to this solution. The solution was stirred at 42° C. until the reaction was deemed to be complete. The solution was added to a solution of potassium bicarbonate (156.7 g, 1565.5 mmol, 5 eq) in water (500 ml) and the resulting mixture was stirred vigorously at 52° C. until the reaction was deemed to be complete. The organic layer was washed with aqueous sodium chloride and concentrated in vacuo to afford a solution of (S)-5-Benzyloxyimino-piperidine-2-carboxylic acid benzyl ester in ethyl acetate.

Propanoic acid (140.6 ml, 1878.6 mmol, 6 eq) was added to a suspension of sodium borohydride (23.2 g, 626.2 mmol, 2 eq) in ethyl acetate (600 ml) and held until the reaction was deemed to be complete. The resulting solution was added to a solution of benzyl (2S)-5-[(benzyloxy)imino]piperidine-2-carboxylic acid benzyl ester in ethyl acetate (600 ml total volume) and sulphuric acid (83.4 ml, 1565 mmol, 5 eq) at −20° C. and held until reaction was deemed to be complete. The reaction was quenched by the addition of water (1000 ml), then neutralized with aqueous ammonia solution. The organic layer was washed with water and concentrated in vacuo to 400 ml. The solution was warmed to 45° C. and held at this temperature. Methanol (200 ml) at 40° C. was added, followed by a freshly prepared solution of oxalic acid dihydrate (39.5 g, 313.1 mmol) in methanol (100 ml). The mixture was cooled and the product was isolated by filtration. The solid was washed with an ethyl acetate/methanol mixture, then with ethyl acetate. The solid was dried to give benzyl (2S,5R)-5-[(benzyloxy)amino]piperidine-2-carboxylate ethanedioate (1:1) as a single isomer (79.4 g, 185 mmol, 59%).

Example 1b

Benzyl (2S,5R)-5-[(benzyloxy)amino]piperidine-2-carboxylate ethanedioate (1:1) was prepared as a single isomer (SR) from a mixture of trans (SR) and cis (SS) isomers using the following procedure.

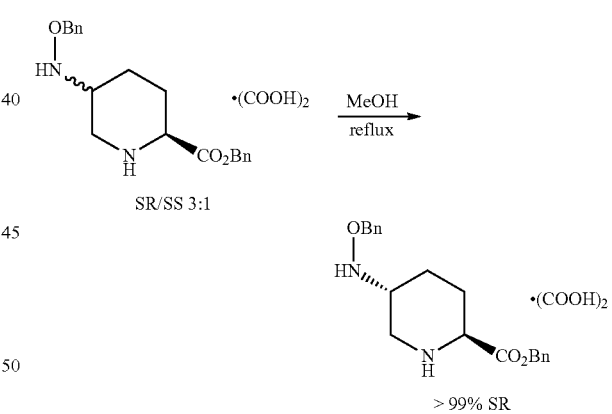

Benzyl (2S,5R)-5-[(benzyloxy)amino]piperidine-2-carboxylate ethanedioate (1:1) (100 g, 233 mmol, 70% SR isomer) was stirred in methanol (1.6 L) and heated to reflux. This temperature was maintained until all solids had dissolved and a clear solution had formed. The solution was cooled to 25° C. over 2 h, and held at this temperature for 2 h. The precipitated solid was isolated by filtration, washed with methanol (200 ml) and dried at 35° C. under vacuum for 16 h, to give benzyl (2S,5R)-5-[(benzyloxy)amino]piperidine-2-carboxylate ethanedioate (1:1) as a white solid (65 g, 65% wt yield).

¹H NMR (400 MHz, DMSO) δ: 1.41 (1H, q), 1.69 (1H, q), 1.88 (1H, d), 2.17 (1H, dd), 2.64 (1H, t), 3.11 (1H, m), 3.40 (1H, d), 4.00 (1H, dd), 4.58 (2H, s), 5.23 (2H, s), 7.35 (10H, m).

Example 1c

Benzyl (2S,5R)-5-[(benzyloxy)amino]piperidine-2-carboxylate ethanedioate (1:1) may be prepared as described in Example 1a except as described below.

Methane sulfonate salt of benzylhydroxylamine is used, causing the process to progress via an alternative intermediate, sulfoxonium oxime. Cyclization is carried out using triethylamine. Piperidine oxime is isolated as its p-toluenesulfonate (tosylate) salt.

Example 1d (2S)-5-benzyloxyamino-piperidine-2-carboxylic acid benzylamide was prepared as outlined below.

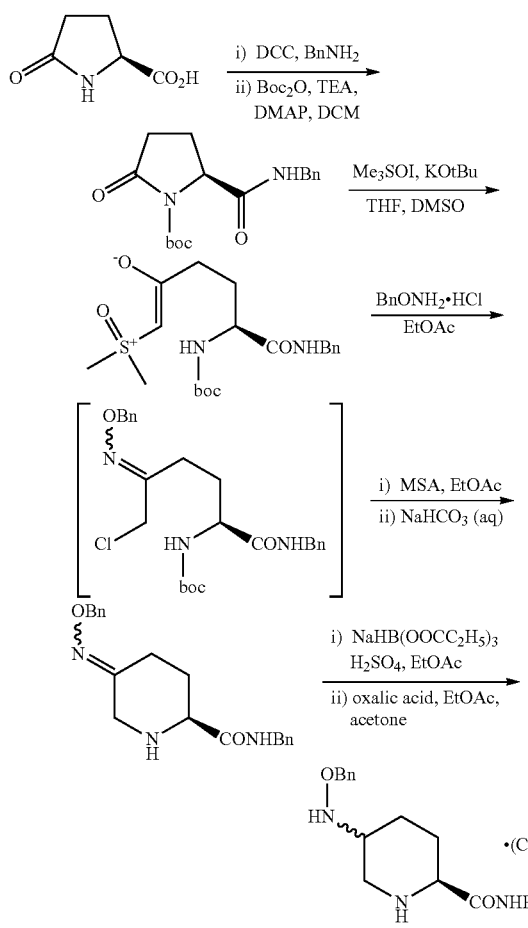

N,N'-Dicyclohexyl carbodiimide (DCC; 8.2 g, 40 mmol) was added to a solution of pyroglutamic acid (5.16 g, 40 mmol) in dimethylformamide (DMF; 60 ml). The mixture was stirred at room temperature for 2 h and a precipitate formed. Benzylamine (4.8 ml, 44 mmol) was added and the mixture was stirred for 2 h. t-butyl dicarbonate (Boc2O; 9.6 g, 44 mmol), triethylamine (TEA; 6.3 ml, 44 mmol) and 4-dimethylaminopyridine (DMAP; 488 mg, 4 mmol) were added and the mixture was stirred at room temperature for 16 h. The DMF was removed under vacuum and the residue was taken up with water (20 ml) and extracted with dichloromethane (DCM; 3×20 ml). The organic layers were concentrated and the crude product was purified via silica gel chromatography to afford (S)-2-benzylcarbamoyl-5-oxo-pyrrolidine-1-carboxylic acid tert-butyl ester (2.23 g, 7.0 mmol, 17.5%).

Dimethylsulfoxide (DMSO; 20 ml) was added dropwise to a suspension of potassium tert-butoxide (1.12 g, 10 mmol) and trimethylsulfoxonium iodide (2.2 g, 10 mmol) in tetrahydrofuran (THF; 15 ml). The mixture was stirred at room temperature for 1 h, then cooled to −10° C. A solution of (S)-2-benzylcarbamoyl-5-oxo-pyrrolidine-1-carboxylic acid tert-butyl ester (1.59 g, 5 mmol) in THF (10 ml) was added, resulting in a white precipitate. The mixture was stirred at 0° C. for 1 h. The reaction was quenched with saturated NH4Cl solution (20 ml), and the product was extracted with EtOAc (2×50 ml). The organic layers were washed with brine and concentrated under vacuum. The product was purified via silica gel chromatography (EtOAc/MeOH) to give the beta-ketosulfoxonium as a white solid (615 mg, 1.5 mmol, 30%).

A slurry of the beta-ketosulfoxonium (584 mg, 1.42 mmol) and O-benzylhydroxylamine (251 mg, 1.57 mmol) in THF (20 ml) was refluxed for 2 h. The mixture was diluted with EtOAc (50 ml) and washed with 1N HCl (20 ml) and brine (20 ml). The product was purified via silica gel chromatography to give the chloro-oxime as a colorless oil (784 mg, quant).

The chloro-oxime oil was dissolved in EtOAc (10 ml) and methane sulfonic acid (320 μl, 4.95 mmol, 3 eq) was added. The mixture was stirred at 40° C. for 3 h. The mixture was poured into saturated sodium bicarbonate solution (10 ml) and stirred at 50° C. for 2 h. The layers were separated and the organic layer was washed with water and concentrated to 10 ml. The solution was cooled to 0° C. Sulfuric acid (447 μl, 8.4 mmol, 5 eq) was added, followed by sodium triacetoxyborohydride (712 mg, 3.36 mmol). The mixture was stirred at 0° C. for 2 h. The reaction was quenched with saturated sodium bicarbonate solution (20 ml). The layers were separated and the organic layer was washed with water. The organic layer was concentrated to 5 ml, and a solution of oxalic acid (153 mg, 1.7 mmol) in ethylacetate (1 ml) and acetone (1 ml) was added. The resulting solid was isolated by filtration, washed with EtOAc and dried under vacuum at 35° C. to afford (2S)-5-benzyloxyamino-piperidine-2-carboxylic acid benzylamide as an off-white solid (430 mg, 1.0 mmol, 71% from BKS N(Bn)).

Example 1e

Benzyl (2S,5R)-5-[(benzyloxy)amino]piperidine-2-carboxylate ethanedioate (1:1) was isolated from a mixture of trans (SR) and cis (SS) isomers using the following procedure.

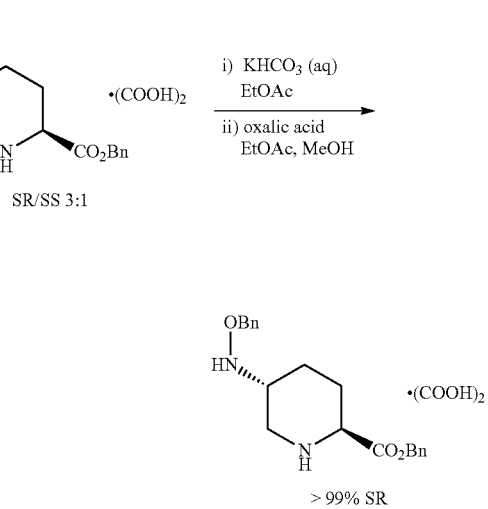

To a slurry of benzyl 5-[(benzyloxy)amino]piperidine-2-carboxylate ethanedioate (1:1) (10 g, 23.3 mmol, 3:1, SR:SS) in ethyl acetate (70 ml) was added a solution of potassium bicarbonate (9.3 g, 93 mmol, 4 eq) in water (90 ml). The mixture was stirred until all the solids had dissolved. The layers were separated and the aqueous layer was extracted with ethyl acetate (30 ml). The combined organic layers were washed with water (50 ml) and concentrated under vacuum below 40° C. to a final volume of 40 ml. The solution was passed through a filter and warmed to 45° C. Methanol (20 ml) at 40° C. was added, followed by a freshly prepared solution of oxalic acid dihydrate (3.67 g, 29.1 mmol) in methanol (10 ml). The mixture was cooled and the product was isolated by filtration. The solid was washed with an ethyl acetate/methanol mixture, then with ethyl acetate. The solid was dried to give benzyl (2S,5R)-5-[(benzyloxy)amino]piperidine-2-carboxylate ethanedioate (1:1) as a single isomer (7.0 g, 16.3 mmol, 70%).

Example 1f

Ethyl (2S,5R)-5-[(benzyloxy)amino]piperidine-2-carboxylate ethanedioate (1:1) was prepared as described below.

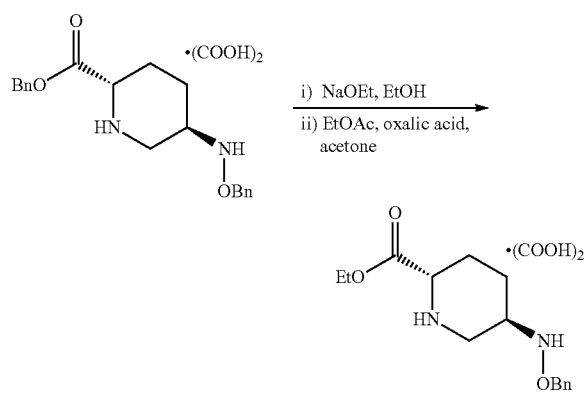

A slurry of benzyl (2S,5R)-5-[(benzyloxy)amino]piperidine-2-carboxylate ethanedioate (1:1) (100 g, 232 mmol) in ethanol (2000 ml) was cooled to 0° C. A solution of sodium ethoxide in ethanol (216 ml, 580 mmol, 21 wt % solution) was added slowly and the mixture was stirred for 1 h at 0° C. Acetic acid (13.3 ml, 232 mmol) was added and the mixture was concentrated under vacuum below 35° C. to a final volume of 300 ml. Ethyl acetate (700 ml) was added and the mixture was concentrated to 300 ml. This procedure was repeated twice. Water (1800 ml) was added to the mixture followed by aqueous ammonia (variable) until the pH of the aqueous layer was 7.5 to 8. The layers were separated and the aqueous layer was extracted with ethyl acetate (2×300 ml). The combined organic layers were washed with water (500 ml) and concentrated to a final volume of 300 ml. The solution was filtered and diluted with ethyl acetate (700 ml) and warmed to 35° C. A solution of oxalic acid dihydrate (30 g, 237 mmol) in acetone (200 ml) was added and the mixture was cooled to room temperature. The solids were isolated by filtration, washed with ethyl acetate and dried under vacuum at 35° C. to obtain ethyl (2S,5R)-5-[(benzyloxy)amino]piperidine-2-carboxylate ethanedioate (1:1) as a white solid (80.7 g, 94%).

Example 1g

Ethyl (2S,5R)-5-[(benzyloxy)amino]piperidine-2-carboxylate ethanedioate (1:1) was prepared as described below.

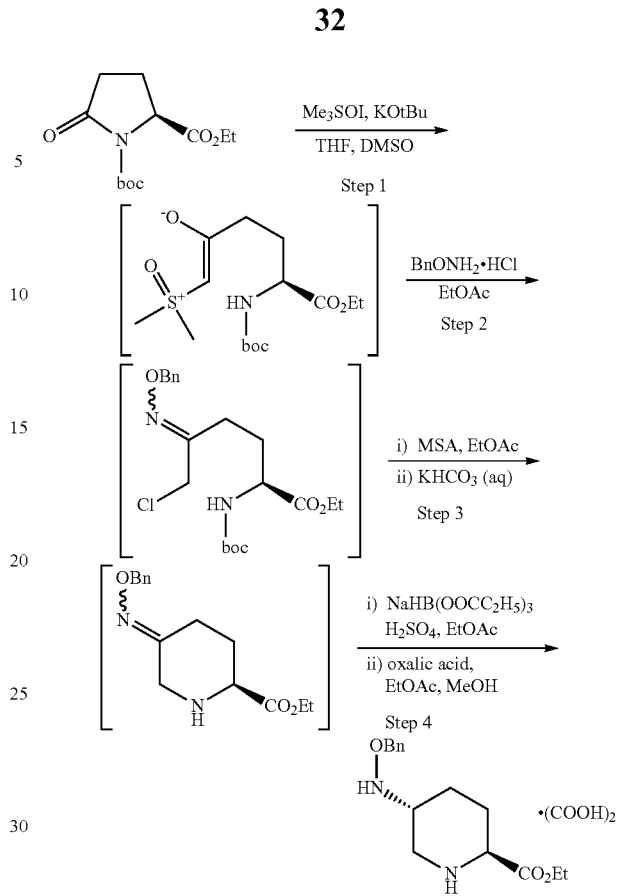

DMSO (120 ml) was added to a mixture of trimethylsulfoxonium iodide (20.5 g, 93.2 mmol, 1.2 eq) and potassium tert-butoxide (10.0 g, 89.4 mmol, 1.15 eq) in tetrahydrofuran (100 ml) at room temperature. The mixture was stirred until the reaction was deemed to be complete and cooled to −12° C. A solution of (S)-5-oxo-pyrrolidine-1,2-dicarboxylic acid 2-ethyl ester 1-tert-butyl ester (20 g, 77.7 mmol, 1 eq) in tetrahydrofuran (60 ml) was added slowly. The mixture was stirred at −12° C. until the reaction was deemed to be complete. The reaction was quenched by the addition of saturated aqueous ammonium chloride (100 ml) and water (60 ml). The product was extracted with ethyl acetate (200 ml), and the resulting organic solution was washed with aqueous sodium chloride. The organic layer was concentrated in vacuo to a final volume of 80 ml.

To this solution was added O-benzylhydroxylamine hydrochloride (13.0 g, 81.6 mmol, 1.05 eq) and ethyl acetate (140 ml). The mixture was stirred at reflux until the reaction was deemed to be complete. The mixture was cooled and washed with water and saturated sodium chloride solution. The organic layer was concentrated in vacuo to 100 ml.

To this solution was added methane sulfonic acid (15.1 ml, 233.1 mmol, 3 eq). The solution was stirred at 42° C. until the reaction was deemed to be complete. The solution was added to a solution of potassium bicarbonate (38.9 g, 388.5 mmol, 5 eq) in water (120 ml) and the resulting mixture was stirred vigorously at 52° C. until the reaction was deemed to be complete. The organic layer was washed with aqueous sodium chloride and concentrated in vacuo to a final volume of 120 ml.

Propanoic acid (34.9 ml, 466.2 mmol, 6 eq) was added to a suspension of sodium borohydride (5.75 g, 155.4 mmol, 2 eq) in ethyl acetate (160 ml) and held until the reaction was deemed to be complete. The resulting solution was added to a solution of (S)-5-Benzyloxyimino-piperidine-2-carboxylic acid ethyl ester in ethyl acetate (120 ml total volume) and sulfuric acid (20.7 ml, 388.5 mmol, 5 eq) at −20° C. and held until reaction was deemed to be complete. The reaction was quenched by the addition of water (240 ml), then neutralized with aqueous ammonia solution. The organic layer was washed with water and concentrated in vacuo to 80 ml. The solution was warmed to 45° C. and held at this temperature. Ethanol (80 ml, 95%) at 40° C. was added, followed by a freshly prepared solution of oxalic acid dihydrate (9.8 g, 77.7 mmol) in ethanol (40 ml). The mixture was cooled and the product was isolated by filtration. The solid was washed with an ethyl acetate/ethanol mixture, then with ethyl acetate. The solid was dried to give ethyl (2S,5R)-5-[(benzyloxy)amino]piperidine-2-carboxylate ethanedioate (1:1) as a single isomer (16.4 g, 44.5 mmol, 57.3%).

$^1$H NMR (400 MHz, DMSO) δ: 1.22 (3H, t), 1.41 (1H, qd), 1.68 (1H, qd), 1.88 (1H, m), 2.13 (1H, dd), 2.65 (1H, t), 3.13 (1H, m), 3.39 (1H, d), 3.92 (1H, dd), 4.19 (2H, q), 4.59 (2H, s), 7.34 (5H, m).

Example 2

Preparation of (2S,5R)-5-[(benzyloxy)amino]piperidine-2-carboxamide

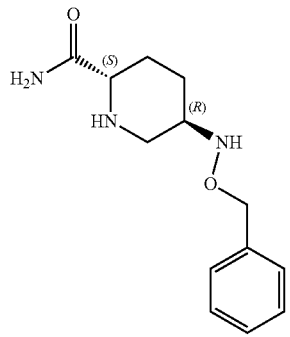

(2S,5R)-5-[(benzyloxy)amino]piperidine-2-carboxamide was prepared as described below.

Example 2a

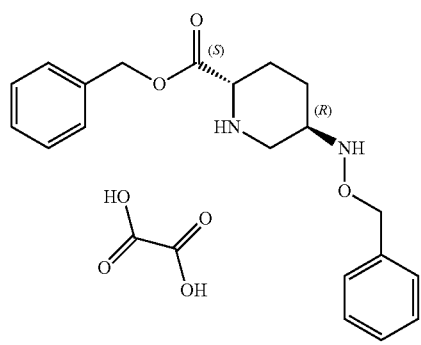

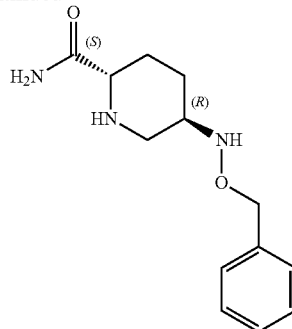

Benzyl (2S,5R)-5-[(benzyloxy)amino]piperidine-2-carboxylate ethanedioate (1:1) (50 g, 113.8 mmol) was mixed with a solution of ammonia in methanol (7N, 700 ml) and agitated until the reaction was deemed to be complete. The mixture was filtered to remove ammonium oxalate byproduct, the ammonium oxalate cake was washed with methanol (2×50 ml) and the combined filtrates were concentrated to 250 ml. Toluene (500 ml) was added and the solution was concentrated to 250 ml causing the product to precipitate. Toluene (500 ml) was added, and the mixture was heated to 80° C. and cooled to 0° C. The product was isolated by filtration, washed with methyl tert-butyl ether (MTBE) (100 ml), and dried to yield a white crystalline solid (26.9 g, 108 mmol, 95%).

$^1$H NMR (400 MHz, DMSO) $δ_H$ 1.12 (1H, m), 1.27 (1H, m), 1.83 (2H, m), 2.22 (1H, dd), 2.76 (1H, m), 2.89 (1H, dd), 3.14 (1H, dd), 4.58 (2H, s), 6.46 (1H, d), 6.91 (1H, s), 7.09 (1H, s), 7.32 (5H, m).

Example 2b

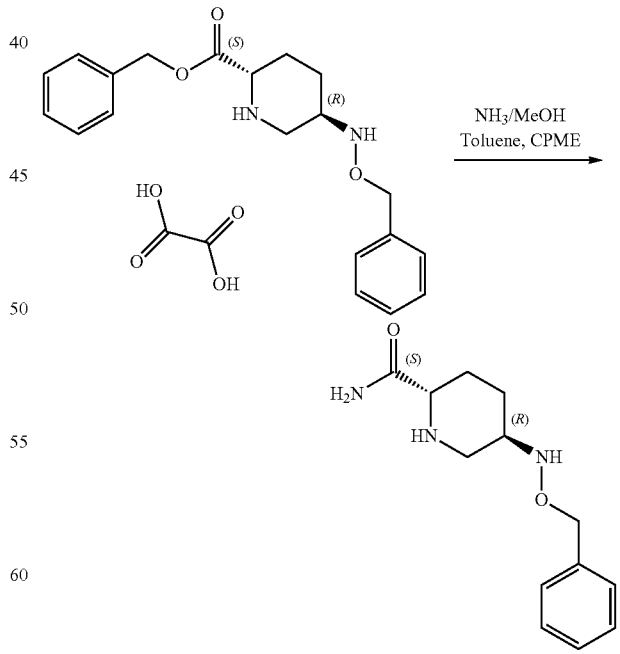

Benzyl (2S,5R)-5-[(benzyloxy)amino]piperidine-2-carboxylate ethanedioate (1:1) (50 g, 113.8 mmol) was mixed with a solution of ammonia in methanol (7N, 700 ml) and agitated at ambient temperature until the reaction was deemed to be complete. The mixture was filtered to remove ammonium oxalate byproduct and washed with methanol (2×50 ml) before being concentrated to 250 ml. Toluene (500 ml) was added and the solution was concentrated to 250 ml causing the product to precipitate. Cyclopentyl methyl ether (CPME) (500 ml) was added and the mixture was heated to 80° C. and then cooled to 0° C. The product was isolated by filtration, washed with CPME (100 ml), and dried to yield a white crystalline solid (26.9 g, 108 mmol, 95%).

Example 2c

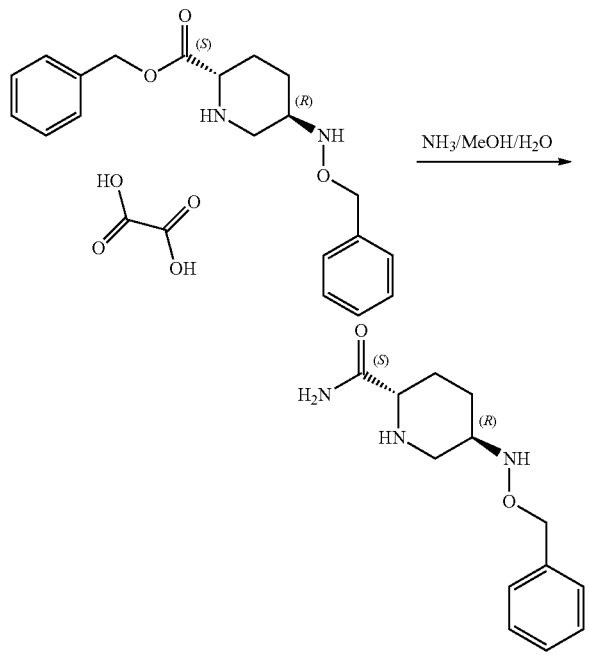

Benzyl (2S,5R)-5-[(benzyloxy)amino]piperidine-2-carboxylate ethanedioate (1:1) (100 g) was mixed with methanol (400 ml) and a solution of aqueous ammonia (35%, 1 L) and agitated until the reaction was deemed to be complete (18 h). The mixture was filtered to remove ammonium oxalate byproduct and concentrated to 500 ml. Saturated aqueous brine solution (1.45 L) was added and mixture cooled to 0° C. The product was isolated by filtration, washed with aqueous saturated brine solution (100 ml) at 0° C., then ice cold water (2×50 ml), then methyl tert-butyl ether (MTBE) (100 ml), and dried to yield a white crystalline solid (38.6 g, 68%).

Example 2d

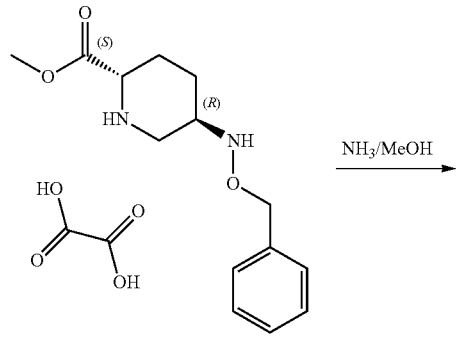

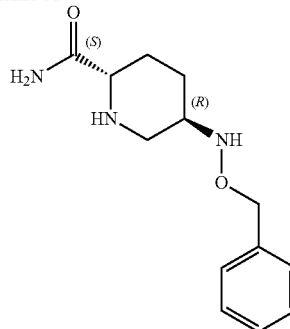

Methyl (2S,5R)-5-[(benzyloxy)amino]piperidine-2-carboxylate ethanedioate (1:1) (1 g, 2.74 mmol) was mixed with a solution of ammonia in methanol (7N, 14 ml) and agitated at ambient temperature until the reaction was deemed to be complete. The mixture was filtered to remove ammonium oxalate byproduct and washed with methanol (2×1 ml) before being concentrated to dryness (0.68 g, 2.72 mmol, 99%).

Example 2e

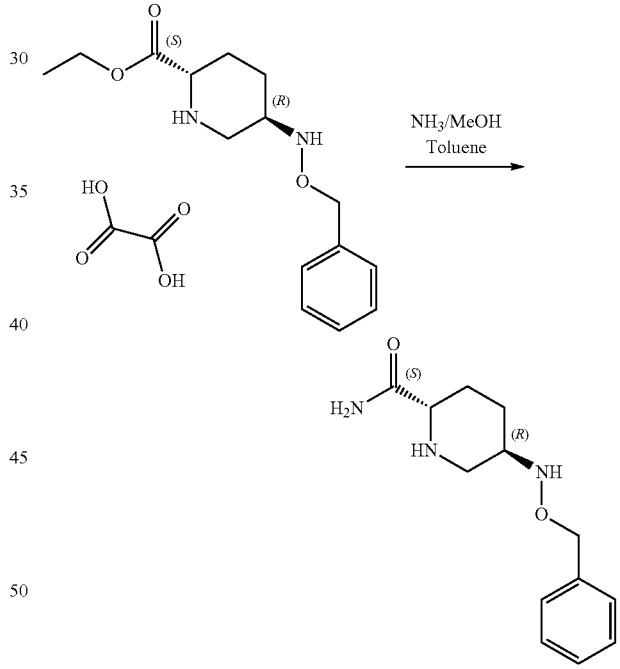

Ethyl (2S,5R)-5-[(benzyloxy)amino]piperidine-2-carboxylate ethanedioate (1:1) (10 g, 27.15 mmol) was mixed with a solution of ammonia in methanol (7N, 140 ml) and agitated at ambient temperature until the reaction was deemed to be complete. The mixture was filtered to remove ammonium oxalate byproduct and washed with methanol (2×50 ml) before being concentrated to 50 ml. Toluene (50 ml) was added and the solution was concentrated to 50 ml causing the product to precipitate. Toluene (50 ml) was added and the mixture was heated to 80° C. and then cooled to 0° C. The product was isolated by filtration, washed with methyl tert-butyl ether (MTBE) (2×15 ml), and dried to yield a white crystalline solid (6.29 g, 25.23 mmol, 93%).

Example 2f (2S,5R)-5-[(benzyloxy)amino]piperidine-2-carboxamide ethanedioate (1:1) was prepared as described below.

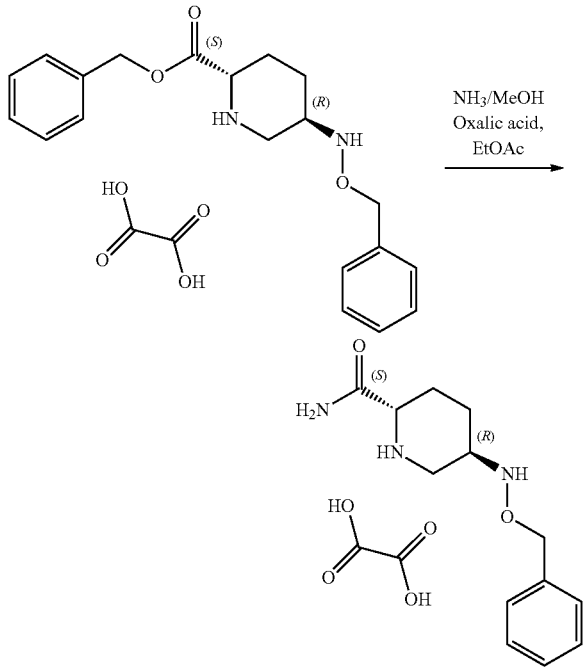

Benzyl (2S,5R)-5-[(benzyloxy)amino]piperidine-2-carboxylate ethanedioate (1:1) (65 g, 148.0 mmol) was mixed with a solution of ammonia in methanol (7N, 910 ml) and agitated at ambient temperature until the reaction was deemed to be complete. The mixture was filtered to remove ammonium oxalate byproduct and washed with methanol (2×65 ml) before being concentrated to 325 ml. Ethyl acetate (325 ml) was added followed by addition of a solution of oxalic acid (dihydrate) (20.52 g) in ethyl acetate (325 ml) and methanol (32.5 ml) to crystallize the product. The product was filtered and washed with ethyl acetate (2×195 ml), then dried to yield a white crystalline solid (49.3 g, 145.2 mmol, 98%).

$^1$H NMR (400 MHz, DMSO+TFA) $\delta_H$ 1.40 (1H, m), 1.61 (1H, m), 1.93 (1H, d), 2.22 (1H, d), 2.76 (1H, m), 3.22 (1H, m), 3.38 (1H, d), 3.70 (1H, t), 4.65 (2H, s), 7.35 (5H, m), 7.62 (1H, s), 7.88 (1H, s).

Example 3

Preparation of (2S,5R)-6-(benzyloxy)-7-oxo-1,6-diazabicyclo[3.2.1]octane-2-carboxamide

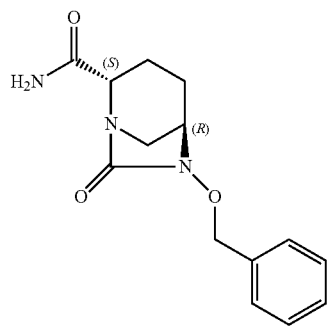

(2S,5R)-6-(benzyloxy)-7-oxo-1,6-diazabicyclo[3.2.1]octane-2-carboxamide was prepared as described below.

Example 3a

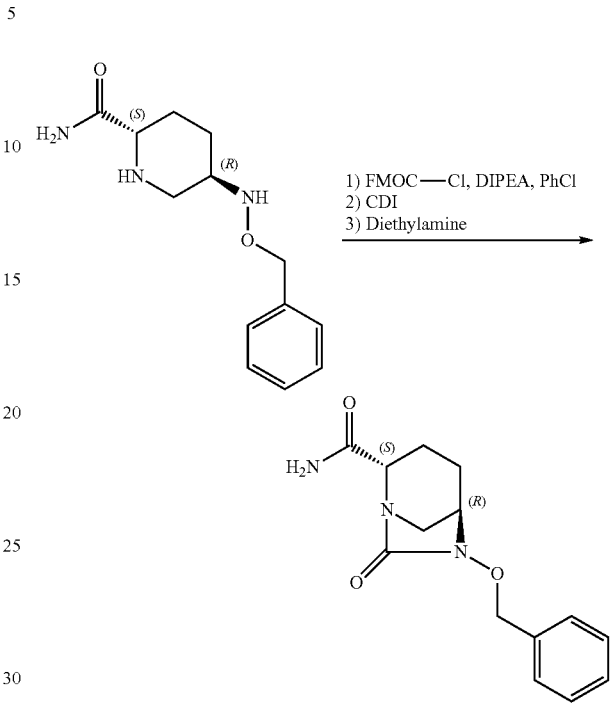

(2S,5R)-5-[(benzyloxy)amino]piperidine-2-carboxamide (102 g, 409 mmol) was mixed with di-isopropylethylamine (76.2 ml, 437.6 mmol) and chlorobenzene (612 ml) at 20° C. 9-fluorenylmethyl chloroformate (107.9 g, 417.2 mmol) as a solution in chlorobenzene (612 ml) was added to the reaction mixture, and the mixture was stirred at 30° C. until the reaction was complete. Carbonyl diimidazole (86.2 g, 531.7 mmol) was added and agitation was continued until the reaction was deemed to be complete. Diethylamine (105.8 ml, 1022.5 mmol) was added and agitation was continued until the reaction was deemed to be complete. Aqueous hydrochloric acid (640 ml, 3N, 1920 mmol) was added and the mixture was cooled to 2° C. The solid was isolated by filtration, washed with water (2×200 ml) and 1-chlorobutane (2×200 mL) and dried to give the title compound as a white crystalline solid (101 g, 367.2 mmol, 90%).

$^1$H NMR (400 MHz, DMSO) $\delta_H$ 1.65 (2H, m), 1.83 (1H, m), 2.07 (1H, m), 2.91 (2H, s), 3.63 (1H, s), 3.69 (1H, d), 4.92 (1H, d), 4.96 (1H, d), 7.38 (7H, m).

Example 3b

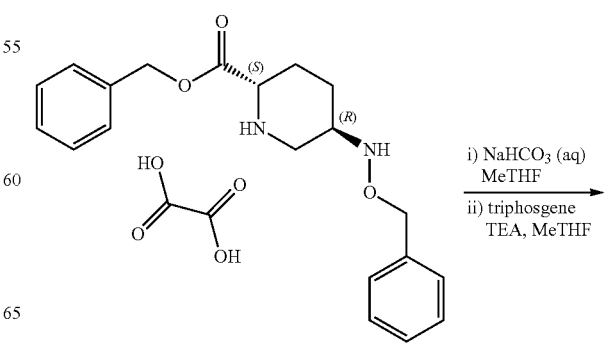

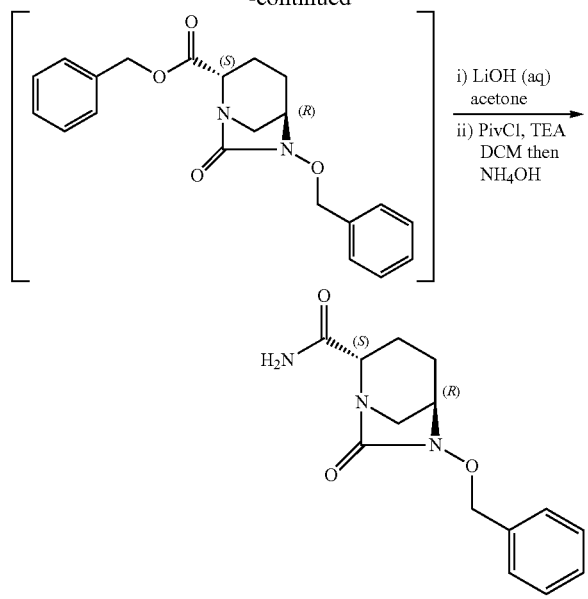

(2S,5R)-6-(benzyloxy)-7-oxo-1,6-diazabicyclo[3.2.1]octane-2-carboxamide was prepared as described below.

A solution of potassium bicarbonate (47.5 g, 475 mmol) in water (250 ml) was added to a suspension of benzyl (2S,5R)-5-[(benzyloxy)amino]piperidine-2-carboxylate ethanedioate (1:1) (50 g, 116 mmol) in 2-methyltetrahydrofuran (350 ml) and water (200 ml). The mixture was stirred until the reaction was deemed to be complete, and the layers were separated. The aqueous layer was extracted with 2-methyltetrahydrofuran (100 ml) and the combined organic layers were washed with water (150 ml). The organic layer was concentrated in vacuo and dried azeotropically to the desired water content. The solution was diluted with 2-methyltetrahydrofuran (800 ml) and cooled to 0° C. Triethylamine (42.4 ml, 309 mmol, 2.67 eq) was added, followed by a solution of triphosgene (15.1 g, 50.8 mmol, 0.44 eq) in 2-methyltetrahydrofuran (200 ml). The mixture was stirred until the reaction was deemed to be complete. The reaction was quenched with a solution of potassium bicarbonate (24 g, 240 mmol, 2.07 eq) in water (300 ml). The layers were separated and the organic layer was washed with aqueous sodium chloride solution. The organic layer was concentrated in vacuo, acetone was added and the solution was concentrated again. The solution was diluted with acetone (final volume 900 ml), water (200 ml) was added, and the mixture was cooled to −12° C. A solution of lithium hydroxide monohydrate (7.8 g, 186 mmol, 1.6 eq) in water (450 ml) was added slowly, and the mixture was stirred until the reaction was deemed to be complete. The reaction was quenched with aqueous hydrochloric acid to a final pH of 8.5. Toluene (500 ml) was added and the layers were separated. The aqueous layer was washed with toluene (2×250 ml). Sodium chloride (60.5 g, 1000 mmol, 8.6 eq) was added, followed by dichloromethane (450 ml). Aqueous hydrochloric acid was added until a final pH of 2.5 was achieved. The layers were separated and the aqueous layer was extracted with dichloromethane (2×150 ml). The combined organic layers were concentrated in vacuo and dried azeotropically. The resulting solution was diluted to 450 ml with dichloromethane and cooled to 0° C. Triethylamine (20 ml, 139 mmol, 1.2 eq) was added, followed by trimethylacetyl chloride (14.2 ml, 116 mmol, 1.0 eq). The mixture was stirred at 0° C. until the reaction was deemed to be complete. The mixture was cooled to −20° C. and quenched with aqueous ammonia (31 ml, 28%, 464 mmol, 4 eq). The mixture was stirred at 0° C. until the reaction was deemed to be complete. Water (250 ml) was added and the layers were separated. The aqueous layer was extracted with dichloromethane (100 ml). The combined organic layers were washed with 2% aqueous ammonium chloride solution (2×250 ml) and concentrated in vacuo. Chlorobutane was added and the solution was concentrated in vacuo. The resulting precipitate was collected by filtration, washed with chlorobutane and dried under vacuum to give (2S,5R)-6-(benzyloxy)-7-oxo-1,6-diazabicyclo[3.2.1]octane-2-carboxamide as a white solid (11.0 g, 40 mmol, 34.5%).

Example 3c

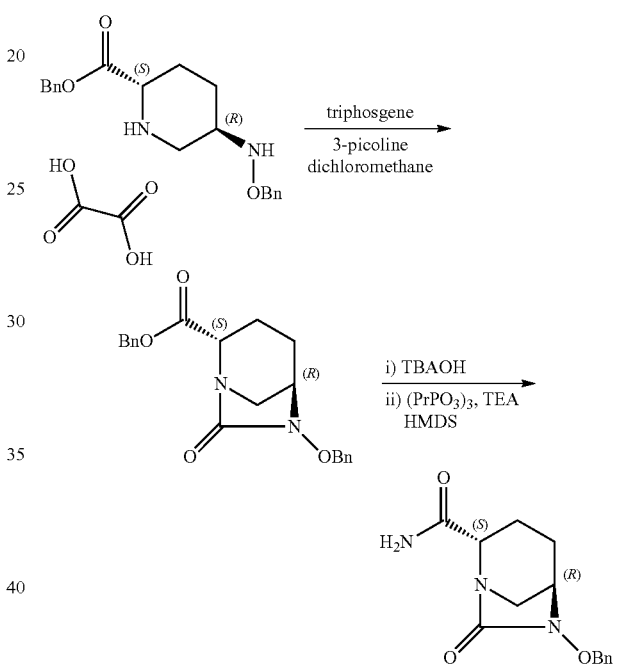

(2S,5R)-6-(benzyloxy)-7-oxo-1,6-diazabicyclo[3.2.1]octane-2-carboxamide was prepared as described below.

3-picoline (45 ml, 464, 4 eq) was added to a slurry of benzyl (2S,5R)-5-[(benzyloxy)amino]piperidine-2-carboxylate ethanedioate (50 g, 116 mmol, 1 eq) in dichloromethane (1000 ml) at 0° C., followed by a solution of triphosgene (31.0 g, 104.4 mmol, 0.9 eq) in dichloromethane (200 ml). The mixture was stirred at 0° C. until the reaction was deemed to be complete. The reaction was quenched with a solution of sodium bicarbonate (24.4 g, 290 mmol, 2.5 eq) in water (300 ml), and the layers were separated. The aqueous layer was extracted with dichloromethane (100 ml) and the combined organic layers were washed with water. The organic layer was concentrated in vacuo to give (2S,5R)-6-benzyloxy-7-oxo-1,6-diaza-bicyclo[3.2.1]octane-2-carboxylic acid benzyl ester as a solution in dichloromethane.

Aqueous tetrabutylammonium hydroxide (116 ml, 1.5 M, 174 mmol, 1.5 eq) was added to this solution at room temperature. The mixture was stirred until the reaction was deemed to be complete. The reaction was quenched with water and the pH was adjusted to 2.5 using HCl. The aqueous layer was extracted and the combined organic layers were washed with water. The organic layer was concentrated in vacuo. Triethylamine (32.3 ml, 232 mmol, 2 eq) and hexamethyldisilazane (72.6 ml, 348 mmol, 3 eq) were added to the resulting solution. A purchased solution of 1-Propanephosphonic acid cyclic anhydride in ethyl acetate (69 ml, 116 mmol, 1 eq, 50 wt % solution) was added to this mixture. The mixture was stirred until the reaction was deemed to be complete. The reaction was quenched with water and the organic layer was washed with aqueous ammonium chloride solution. The organic layer was concentrated in vacuo. Chlorobutane was added and the solution was concentrated again causing the product to crystallize. The solid was isolated by filtration, washed with chlorobutane and dried under vacuum to give (2S,5R)-6-(benzyloxy)-7-oxo-1,6-diazabicyclo[3.2.1]octane-2-carboxamide as a white solid (22.3 g, 81.1 mmol, 70%).

Example 3d

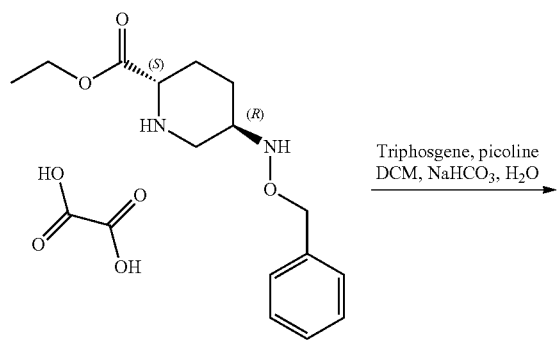

(2S,5R)-6-(benzyloxy)-7-oxo-1,6-diazabicyclo[3.2.1]octane-2-carboxamide may be prepared using an enzymatic approach as described below.

3-picoline (52.6 ml, 543 mmol, 4 eq) was added to a slurry of ethyl (2S,5R)-5-[(benzyloxy)amino]piperidine-2-carboxylate ethanedioate (1:1) (50 g, 136 mmol, 1 eq) in dichloromethane (1000 ml) at 0° C., followed by a solution of triphosgene (36.4 g, 122.4 mmol, 0.9 eq) in dichloromethane (200 ml). The mixture was stirred at 0° C. until the reaction was deemed to be complete. The reaction was quenched with a solution of sodium bicarbonate (28.6 g, 340 mmol, 2.5 eq) in water (300 ml), and the layers were separated. The aqueous layer was extracted with dichloromethane (100 ml) and the combined organic layers were washed with water. The organic layer was concentrated in vacuo to give (2S,5R)-6-benzyloxy-7-oxo-1,6-diaza-bicyclo[3.2.1]octane-2-carboxylic acid ethyl ester as a solution in dichloromethane (solution yield: 35 g, 116 mmol, 85%). Acetonitrile was added and the solution was concentrated in vacuo to give (2S,5R)-6-benzyloxy-7-oxo-1,6-diaza-bicyclo[3.2.1]octane-2-carboxylic acid ethyl ester as a solution in acetonitrile. This solution was diluted with acetonitrile to 700 ml. To this was added ammonium carbamate (11.3 g, 145 mmol, 1.25 eq) and Novozyme 435 (35 g, immobilized *Candida antarctica* lipase B). The mixture was stirred at 40° C. until the reaction was deemed to be complete. The reaction mixture was filtered and concentrated in vacuo. The solution was diluted with dichloromethane, washed with aqueous ammonium chloride, and concentrated in vacuo. Chlorobutane was added and the solution was concentrated in vacuo. The precipitate was isolated by filtration, washed with chlorobutane and dried to give 2S,5R)-6-(benzyloxy)-7-oxo-1,6-diazabicyclo[3.2.1]octane-2-carboxamide as a white solid (24.3 g, 88 mmol, 65% from ethyl (2S,5R)-5-[(benzyloxy)amino]piperidine-2-carboxylate ethanedioate).

Example 3e (2S,5R)-6-(benzyloxy)-7-oxo-1,6-diazabicyclo[3.2.1]octane-2-carboxamide was prepared as described below.

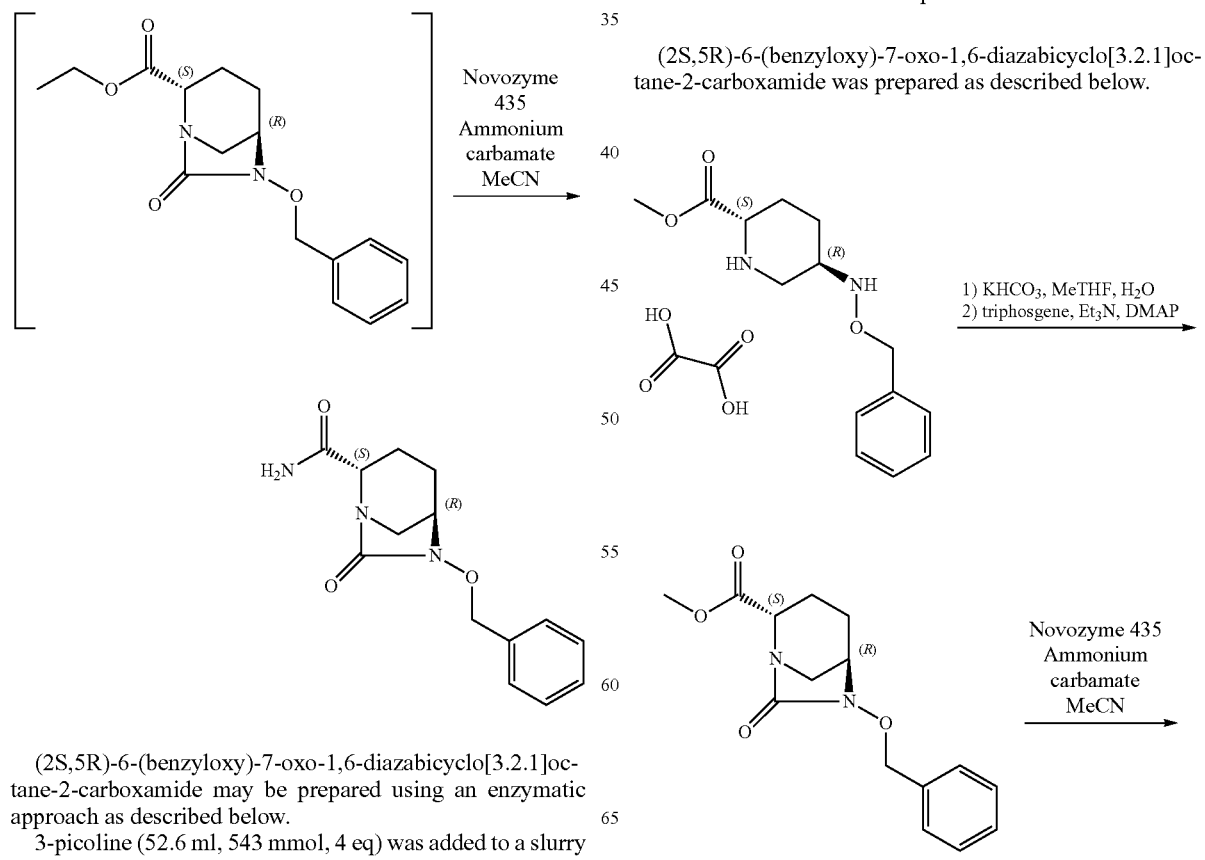

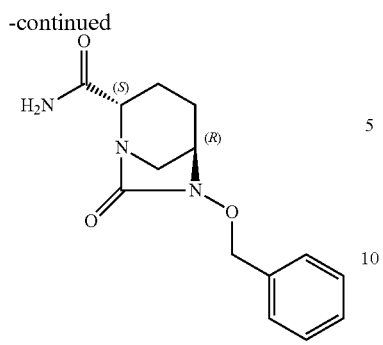

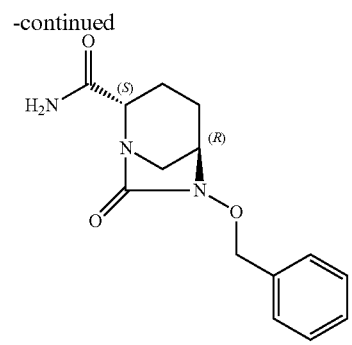

Saturated aqueous potassium bicarbonate (30 ml) was added to a solution of methyl (2S,5R)-5-[(benzyloxy)amino] piperidine-2-carboxylate ethanedioate (1:1) (3.0 g, 8.38 mmol) in 2-methyltetrahydrofuran (25 ml). The layers were separated and the organic phase was washed with saturated aqueous sodium chloride solution (12.5 ml). The aqueous phase was back extracted with 2-methyltetrahydrofuran (8.4 ml). The combined organic phases were concentrated to dryness, then reconstituted in 2-methyltetrahydrofuran (75 ml). Triethylamine (3.1 ml) was added and the solution was cooled to −5° C. Triphosgene (1.1 g) in 2-methyltetrahydrofuran (16.8 ml) was added dropwise, maintaining a temperature <−3° C. The mixture was stirred for 1 hour before dimethylaminopyridine (102 mg) was added. The mixture was held until the reaction was deemed to be complete. The reaction was quenched with saturated aqueous potassium bicarbonate (21 ml). The layers were separated and the organic phase was washed with water (12.6 ml). Each aqueous layer was back extracted with 2-methyltetrahydrofuran (12.6 ml). The combined organics were evaporated to dryness (3.51 g).

(2S,5R)-6-benzyloxy-7-oxo-1,6-diaza-bicyclo[3.2.1]octane-2-carboxylic acid methyl ester (0.767 g) was dissolved in acetonitrile (15.5 mL) containing ammonium carbamate (200 mg), Novozyme 435 (0.770 g, immobilized *Candida antarctica* lipase B) and calcium dichloride (0.244 g). Ascarite II (2.4 g) was charged separately to the headspace. The mixture was stirred at 40° C. until the reaction was deemed to be complete. The reaction mixture was filtered and concentrated in vacuo, before adding chlorobutane. The precipitate was isolated by filtration in a centrifuge, washed with chlorobutane and dried to give 2S,5R)-6-(benzyloxy)-7-oxo-1,6-diazobicyclo[3.2.1]octane-2-carboxamide as a white solid (96% HPLC area).

Example 3f (2S,5R)-6-(benzyloxy)-7-oxo-1,6-diazabicyclo[3.2.1]octane-2-carboxamide was prepared using N,N-Carbonyl diimidazole (CDI) as described below.

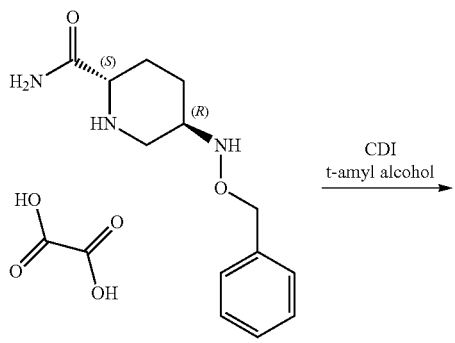

(2S,5R)-5-[(benzyloxy)amino]piperidine-2-carboxamide (2 g) was mixed with t-amyl alcohol (60 ml) and heated to 40° C. N,N-carbonyl diimidazole (CDI) (3.9 g) was added in portions over 1 hour and then the mixture heated to 60° C. for 1 hour before concentrating under vacuum to approximately half its volume. The mixture was cooled to 0° C., seeded, and held at 0° C. for 1.5 hours. The mixture was then filtered and washed with MTBE (5 ml) before drying at 40° C. to yield a white crystalline solid (1.25 g, 56%)

Example 3g (2S,5R)-6-(benzyloxy)-7-oxo-1,6-diazabicyclo[3.2.1]octane-2-carboxamide was prepared as described below.

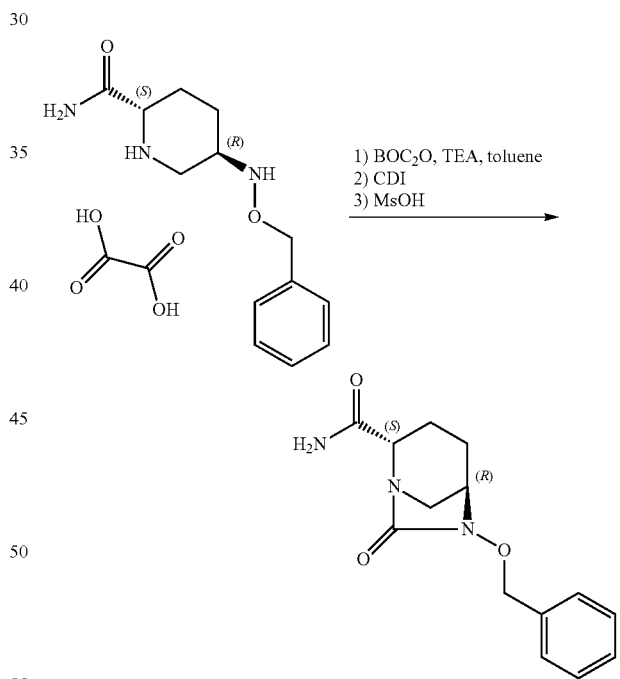

(2S,5R)-5-[(benzyloxy)amino]piperidine-2-carboxamide (291 mg, 1.17 mmol) was mixed with triethylamine (193 l, 1.37 mmol) and toluene (2.4 ml) at 20° C. di-t-butyldicarbonate (310 mg, 1.42 mmol) as a solution in toluene (2.0 ml) was added to the reaction mixture, and the mixture was stirred at 40° C. until the reaction was complete. The solution was diluted with toluene (3.9 mL) and carbonyl diimidazole (462 mg, 2.85 mmol) was added and agitation was continued until the reaction was deemed to be complete. Methanesulfonic acid (663 l, 10.2 mmol) was added and agitation was continued until the reaction was deemed to be complete. After lowering the temperature to 20° C., aqueous potassium hydrogen carbonate (10.2 ml, 1N, 10.2 mmol) was added and the mixture was stirred at 20° C. until the reaction was complete. The aqueous layer was separated and the toluene layer washed with water (3 mL), citric acid (1N, 3 mL) and water (3 mL). The four aqueous washes were twice back-extracted with dichloromethane (2×3 mL). The three organic extracts were combined to give (2S,5R)-6-(benzyloxy)-7-oxo-1,6-diazabicyclo[3.2.1]octane-2-carboxamide as a solution in toluene and dichloromethane (176 mg, 0.64 mmol, 55%).

Example 4

Preparation of tetrabutylammonium ({[(2S,5R)-2-carbamoyl-7-oxo-1,6-diazabicyclo[3.2.1]oct-6-yl]oxy}sulphonyl]oxidanide

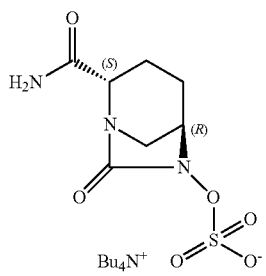

Example 4a

Tetrabutylammonium ({[(2S,5R)-2-carbamoyl-7-oxo-1,6-diazabicyclo[3.2.1]oct-6-yl]oxy}sulphonyl]oxidanide was prepared as described below.

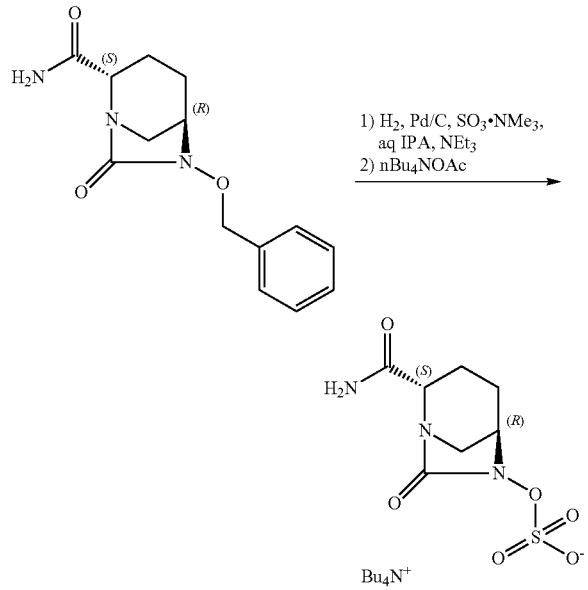

(2S,5R)-6-(benzyloxy)-7-oxo-1,6-diazabicyclo[3.2.1]octane-2-carboxamide (10 g, 36.2 mmol, 1 eq) was mixed with sulfur trioxide trimethylamine complex (6.07 g, 43.44 mmol, 1.2 eq), triethylamine (1.3 ml, 18 mmol, 0.25 eq), palladium on carbon (0.8 g, 10% palladium, 50% water), isopropanol (50 ml) and water (50 ml). This mixture was treated with hydrogen until the reaction was deemed to be complete. The catalyst was removed by filtration and washed with water (20 ml). The combined filtrates were washed with n-BuOAc (70 ml, 20 ml) before a solution of tetrabutylammonium acetate (54.5 mmol) in water (20 ml) was added. The product was extracted with dichloromethane (100 ml, 50 ml) and solvent swapped into 4-methyl-2-pentanone, before filtering, washing and drying to yield a white crystalline solid (16.9 g, 92%).

$^1$H NMR (400 MHz, CDCl3) $\delta_H$ 1.00 (12H, t), 1.45 (8H, m), 1.67 (9H, m), 1.87 (1H, m), 2.16 (1H, m), 2.37 (1H, dd), 2.87 (1H, d), 3.31 (9H, m), 3.91 (1H, d), 4.33 (1H, s), 5.79 (1H, s), 6.67 (1H, s).

Example 4b

Tetrabutylammonium ({[(2S,5R)-2-carbamoyl-7-oxo-1,6-diazabicyclo[3.2.1]oct-6-yl]oxy}sulphonyl]oxidanide was prepared as described below.

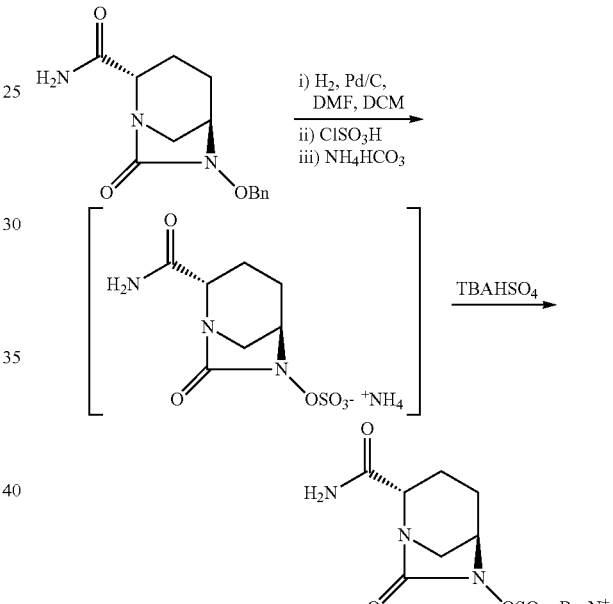

Palladium on carbon (400 mg, 5% Pd, 3% water) was added to a solution of (2S,5R)-6-(benzyloxy)-7-oxo-1,6-diazabicyclo[3.0.1]octane-2-carboxamide (10.0 g, 36.2 mmol) in dimethylformamide (50 ml) and dichloromethane (50 ml). The mixture was stirred under hydrogen atmosphere (3 atm) until the reaction was deemed to be complete. The catalyst was removed by filtration and washed with a dimethylformamide/dichloromethane mixture (1:1, 40 ml). The combined filtrates were added to a solution of chlorosulfonic acid (7.26 ml, 109.2 mmol 3 eq) in dimethylformamide (20 ml) and dichloromethane (20 ml) at 20° C. The reaction mixture was stirred until the reaction was deemed to be complete. The solution was added to ammonium bicarbonate (28.8 g, 364 mmol, 10 eq) in water (80 ml) maintaining a pH>6. Dichloromethane (50 ml) was added and the layers were separated. The aqueous layer was washed with dichloromethane (2×100 ml). A solution of ammonium bicarbonate (5.75 g, 72.8 mmol, 2 eq) in water (60 ml) was added, followed by a solution of tetrabutylammonium bisulfate (18.5 g, 54.6 mmol, 1.5 eq) in dichloromethane (100 ml). The layers were separated and the aqueous layer was extracted with dichloromethane (50 ml). The combined organic layers were washed with water (50 ml) and concentrated in vacuo. 2-methylpentan-4-one was added and the solution was concentrated in vacuo. The precipitate was collected by filtration, washed with 2-methylpentan-4-one and dried under vacuum to give tetrabutylammonium ({[(2S,5R)-2-carbamoyl-7-oxo-1,6-diazabicyclo[3.2.1]oct-6-yl]oxy}sulphonyl]oxidanide as a white solid (11.14 g, 22 mmol, 60%).

Example 4c

Tetrabutylammonium ({[(2S,5R)-2-carbamoyl-7-oxo-1,6-diazabicyclo[3.2.1]oct-6-yl]oxy}sulphonyl]oxidanide was prepared as described below.

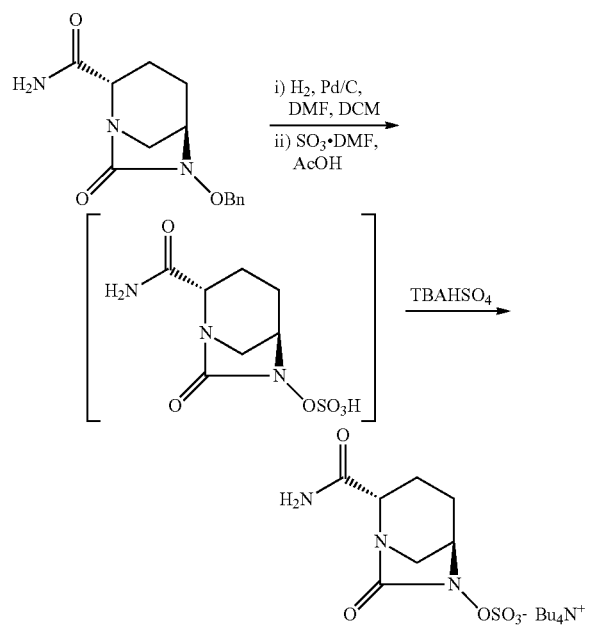

Palladium on carbon (1 g, 5% Pd, 3% wet) was added to a solution of (2S,5R)-6-(benzyloxy)-7-oxo-1,6-diazabicyclo[3.2.1]octane-2-carboxamide (5 g, 18.2 mmol) in dimethylformamide (25 ml) and dichloromethane (50 ml). The mixture was stirred under a hydrogen atm (3 bar) until the reaction was deemed to be complete. The catalyst was removed by filtration and washed with a mixture of dimethylformamide (5 ml) and dichloromethane (10 ml). The combined filtrates were added to a solution of SO3.DMF (5.58 g, 36.4 mmol) in acetic acid (20 ml). The mixture was stirred until the reaction was deemed to be complete. Dichloromethane (100 ml) was added and the resulting precipitate was collected by filtration. The precipitate was washed with dichloromethane (2×10 ml). A solution of tetrabutylammonium acetate in water (23.7 ml, 1M, 23.7 mmol, 1.3 eq) was added to the precipitate. The product was extracted with dichloromethane (50 ml, 10 ml), and the combined organic layers were washed with water (10 ml). The organic layer was concentrated, diluted with 4-methyl-2-pentanone and concentrated again. The resulting precipitate was collected by filtration, washed with cold 4-methyl-2-pentanone and dried under vacuum to give tetrabutylammonium ({[(2S,5R)-2-carbamoyl-7-oxo-1,6-diazabicyclo[3.2.1]oct-6-yl]oxy}sulphonyl]oxidanide as a white solid (6.33 g, 69%).

Example 4d

Tetrabutylammonium ({[(2S,5R)-2-carbamoyl-7-oxo-1,6-diazabicyclo[3.2.1]oct-6-yl]oxy}sulphonyl]oxidanide was prepared as described below.

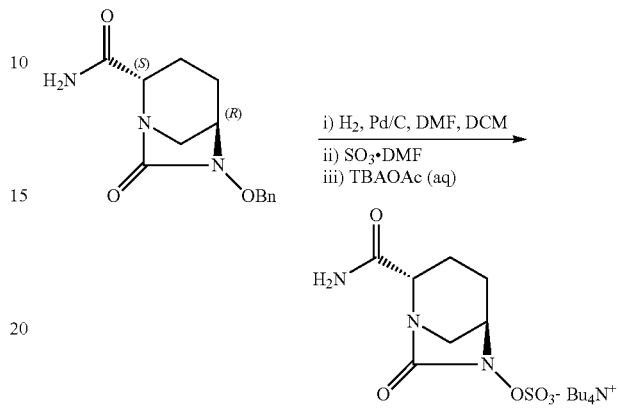

A mixture of (2S,5R)-6-(benzyloxy)-7-oxo-1,6-diazabicyclo[3.2.1]octane-2-carboxamide (10 g, 36.3 mmol), Pd/C (10%, 2 g, 0.2 parts), dichloromethane (50 ml) and dimethylformamide (50 ml) is stirred in a hydrogen atmosphere (3 bar) for 3 h. The catalyst is removed by filtration through a cellulose pad and washed with DMF (20 ml). To the combined filtrates is added a solution of SO3.DMF (5.07 g, 35.6 mmol) in DMF (15 ml). The mixture is stirred for 30 min at room temperature. The reaction mixture is analyzed by HPLC for consumption of the starting material. If necessary, additional SO3.DMF in DMF is added and the mixture is stirred a further 30 min. On completion of the reaction, the mixture is quenched by the addition of a solution of tetrabutylammonium acetate (15 g, 49.8 mmol) in water (50 ml). The mixture is stirred for 2 h at room temperature. Xylenes (400 ml) is added and the mixture is concentrated under vacuum below 35° C. to a final volume of 50 ml. Xylenes (400 ml) is added and the mixture is concentrated to a final volume of 35 ml. Water (20 ml) is added and the mixture is allowed to settle. The organic layer is removed. The aqueous layer is extracted with DCM (3×50 ml) and the combined organic layers are washed with water (10 ml). The organic layer is treated with SC-40 carbon at reflux to remove palladium impurities. The carbon is removed by filtration. The organic layer is concentrated under vacuum to a final volume of 50 ml. MIBK (50 ml) is added, and the mixture is concentrated to a final volume of 50 ml. MIBK (130 ml) is added and the mixture is concentrated to a final volume of 90 ml. The mixture is cooled to 0° C. and stirred for 3 h. The crystals are collected by filtration, washed with cold MIBK (20 ml) and dried under vacuum at 45° C. to afford tetrabutylammonium ({[(2S,5R)-2-carbamoyl-7-oxo-1,6-diazabicyclo[3.2.1]oct-6-yl]oxy}sulphonyl]oxidanide (11.2 g, 61%).

Example 4e

Tetrabutylammonium ({[(2S,5R)-2-carbamoyl-7-oxo-1,6-diazabicyclo[3.2.1]oct-6-yl]oxy}sulphonyl]oxidanide was prepared as described below.

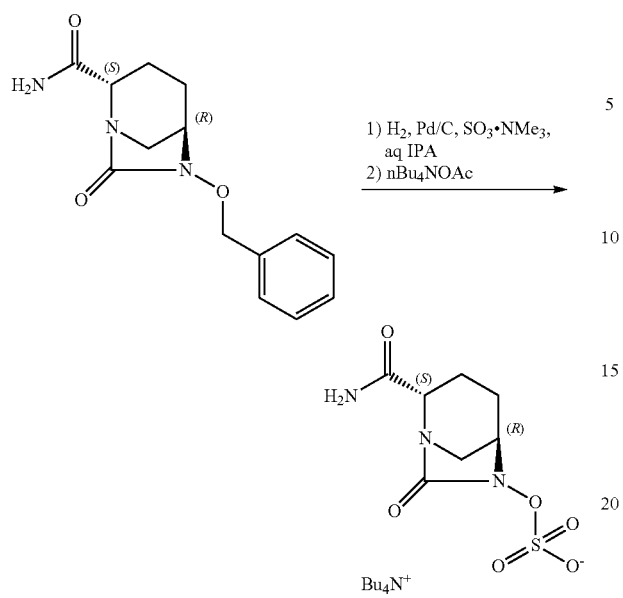

(2S,5R)-6-(benzyloxy)-7-oxo-1,6-diazabicyclo[3.2.1]octane-2-carboxamide (60 g, 215.8 mmol, 1 eq) was mixed with sulfur trioxide trimethylamine complex (36.0 g, 258.9 mmol, 1.2 eq), triethylamine (7.52 ml, 53.9 mmol, 0.25 eq), palladium on carbon (2.4 g, 10% palladium, 50% water), isopropanol (300 ml) and water (300 ml). This mixture was then held under hydrogen (1 bar) until the reaction was deemed to be complete. The catalyst was removed by filtration and washed with isopropanol (120 ml). The combined filtrates were added to a pre-mixed solution of tetrabutylammonium hydroxide (118 mmol, 1.15 eq), acetic acid (15.45 mL, 270 mmol, 1.25 eq) and water (120 ml). The product solution was concentrated by distillation to remove isopropanol, and the product was extracted with dichloromethane (360 ml, 120 ml) and solvent swapped into 4-methyl-2-pentanone, before filtering, washing and drying to yield a white crystalline solid (90.4 g, 79%).

Example 5

Preparation of Sodium ({[(2S,5R)-2-carbamoyl-7-oxo-1,6-diazabicyclo[3.2.1]oct-6-yl]oxy}sulphonyboxidanide (NXL-104)

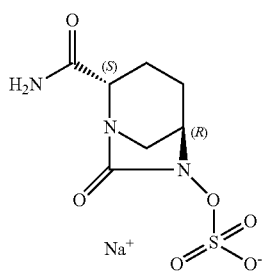

Sodium ({[(2S,5R)-2-carbamoyl-7-oxo-1,6-diazabicyclo[3.2.1]oct-6-yl]oxy}sulphonyl)oxidanide was prepared as described below.

Example 5a

Sodium ({[(2S,5R)-2-carbamoyl-7-oxo-1,6-diazabicyclo[3.2.1]oct-6-yl]oxy}sulphonyl]oxidanide (NXL-104 Form I) was prepared as described below.

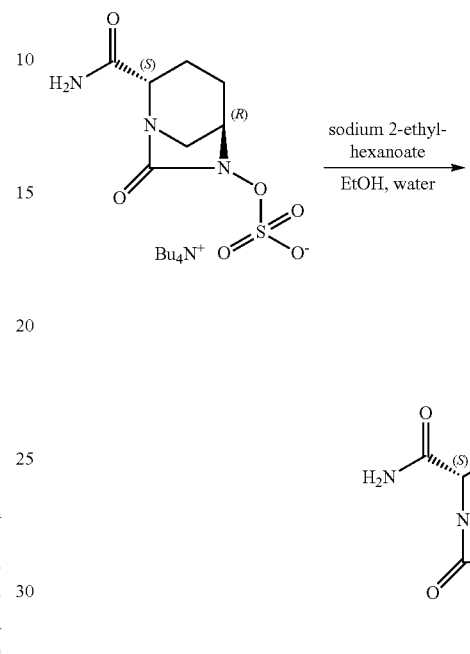

A solution of sodium ethyl hexanoate (32.8 g, 197 mmol, 2 eq) in ethanol (350 ml) was added to a seeded solution of tetrabutylammonium ({[(2S,5R)-2-carbamoyl-7-oxo-1,6-diazabicyclo[3.2.1]oct-6-yl]oxy}sulphonyl]oxidanide (50 g, 98.7 mmol) in ethanol (315 ml) containing water (6.25 ml, 2% by volume). The reaction mixture was held until reaction was deemed to be complete. The product was filtered, washed and dried to yield a white crystalline solid (26.6 g, 94%).

$^1$H NMR (400 MHz, CDCl3) $\delta_H$ 1.65 (2H, m), 1.84 (1H, m), 2.07 (1H, m), 2.93 (1H, d), 3.03 (1H, d), 3.69 (1H, d), 3.99 (1H, s), 7.27 (1H, s), 7.43 (1H, s).

Example 5b

Sodium ({[(2S,5R)-2-carbamoyl-7-oxo-1,6-diazabicyclo[3.2.1]oct-6-yl]oxy}sulphonyl]oxidanide (NXL-104 Form II) was prepared as described below

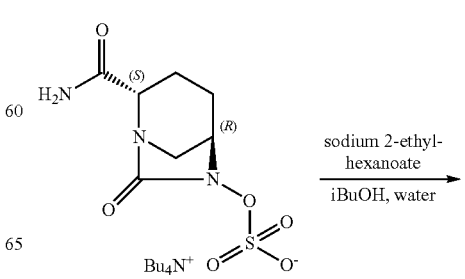

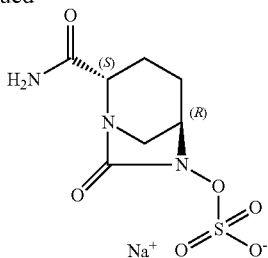

A solution of tetrabutylammonium ({[(2S,5R)-2-carbamoyl-7-oxo-1,6-diazabicyclo[3.2.1]oct-6-yl]oxy}sulphonyl]oxidanide (10.1 g, 20 mmol) in isobutanol (48 ml) and water (2.5 ml) was transferred to a 500 ml reactor via a 0.2 μm filter and warmed to 35° C. Separately, sodium 2-ethylhexanoate (6.7 g) was dissolved in isobutanol (49.5 ml) and water (0.5 ml) at 35° C. This solution was added to the solution of tetrabutylammonium ({[(2S,5R)-2-carbamoyl-7-oxo-1,6-diazabicyclo[3.2.1]oct-6-yl]oxy}sulphonyl]oxidanide via a 0.2 μm filter over 1 h. The mixture was stirred 1 h at 35° C., 2 h at 25° C. and 2 h at 0° C. The mixture was filtered and the crystals were washed with a mixture of isobutanol (19.5 ml) and water (0.5 ml). The crystals were dried under vacuum at 35° C. to afford a crystalline form (5.48 g, 90%).

Example 5c

Sodium ({[(2S,5R)-2-carbamoyl-7-oxo-1,6-diazabicyclo[3.2.1]oct-6-yl]oxy}sulphonyl]oxidanide (NXL-104 Form I) was prepared as described below.

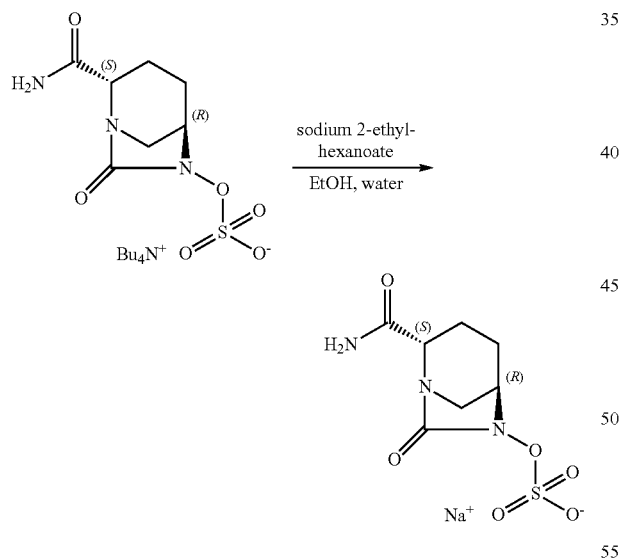

A solution of tetrabutylammonium ({[(2S,5R)-2-carbamoyl-7-oxo-1,6-diazabicyclo[3.2.1]oct-6-yl]oxy}sulphonyl]oxidanide (50 g, 98.7 mmol) in isobutanol (238 ml) and water (12.5 ml) was transferred to a 1-liter reactor via a 0.2 μm filter and warmed to 35° C. Separately, a sodium 2-ethylhexanoate (33.3 g) was dissolved in isobutanol (250 ml) at 35° C. This solution was added to the solution of tetrabutylammonium ({[(2S,5R)-2-carbamoyl-7-oxo-1,6-diazabicyclo[3.2.1]oct-6-yl]oxy}sulphonyl]oxidanide over 1 h. The mixture was stirred 1 h at 35° C., 2 h at 25° C. and 2 h at 0° C. The mixture was filtered and the crystals are washed with a mixture of isobutanol (97.5 ml) and water (2.5 ml). The crystals were resuspended in anhydrous EtOH (250 ml) and stirred at 35° C. for 4 h. The mixture was cooled to 0° C. and filtered. The crystals were washed with EtOH (25 ml) and dried at 35° C. for 16 h to give 26.2 g (93%) of NXL-104 as a fine white powder. XRD shows pure Form I. HELOS $X_{50}$=4.6 μm.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

All patents, patent applications, publications, product descriptions, and protocols are cited throughout this application, the disclosures of which are incorporated herein by reference in their entireties for all purposes.

What is claimed is:
1. A process for preparing a compound of Formula (I):

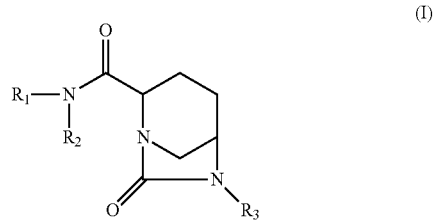

or a pharmaceutically acceptable salt, solvate, hydrate, enantiomer or diastereomer thereof; comprising
(a) treating a compound of Formula (II):

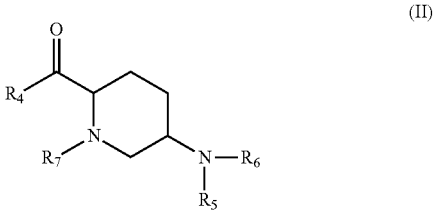

with a source of nitrogen or an amine to prepare a compound of Formula (III):

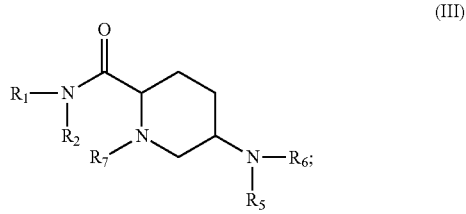

and
(b) treating the compound of Formula (III) with a protecting group and a carbonylation agent; wherein
R1, R2, R3, R4, R5, R6 and R7 are identical or different and are independently selected from the group consisting of hydrogen, oxygen, nitrogen, amino, carbonyl, carbamoyl, alkyl, alkenyl, alkynyl, alkoxy, cycloalkyl, aryl, aralkyl, trialkylsilyl and heterocycle; wherein each of R1 R2, R3, R4, R5, R6 and R7 is optionally substituted by one or more halogen, oxygen, hydroxy, cyano, nitro, amino, alkyl amino, dialkylamino, arylamino, diarylamino, amido, alkylamido, carbamoyl, ureido, dimethyl amino, carboxyl, alkyl, allyl, halogenated alkyl, trialkylsilyl, alkenyl, alkynyl, cyclo alkyl, cycloalkylalkyl, aryl, arylalkyl, hetero aryl, heteroarylalkyl, heterocycle, hetero cycle alkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl, alkoxycarbonyl, aryloxycarbonyl, heteroaryloxycarbonyl or a combination thereof; or R1 and R2 together form a heterocycle; optionally substituted by one or more halogen, hydroxy, cyano, nitro, amino, alkyl amino, dialkylamino, arylamino, diarylamino, amido, alkylamido, carbamoyl, ureido, dimethylamino, carboxyl, alkyl, halogenated alkyl, alkenyl, alkynyl, cycloalkyl, cycloalkylalkyl, aryl, arylalkyl, hetero aryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkylthio, arylthio, alkylsulfinyl, alkylsulfonyl, arylsulfinyl, arylsulfonyl, heteroarylsulfinyl, heteroarylsulfonyl alkoxycarbonyl, aryloxycarbonyl, heteroaryloxycarbonyl or a combination thereof; or R3, R5 and R6 are independently COH, COB', COOB', $CONH_2$, CONHB', CONHOH, $CONHSO_2B'$, $CH_2COOH$, $CH_2COOB'$, $CH_2CONHOH$, $CH_2CONHCN$, $CH_2$tetrazole, protected $CH_2$tetrazole, $CH_2SO_3H$, $CH_2SO_2B'$, $CH_2PO(OB')_2$, $CH_2PO(OB')(OH)$, $CH_2PO(B')(OH)$ and $CH_2PO(OH)_2$; wherein B' is selected from the group consisting of 25 alkyl containing 1 to 6 carbon atoms optionally substituted by a pyridyl or carbamoyl radical, —CHz-alkenyl containing 3 to 9 carbon atoms, aryl containing 6 to 10 carbon atoms and aralkyl containing 7 to 11 carbon atoms, wherein the nucleus of said aryl or aralkyl is optionally substituted by OH, $NH_2$, $NO_2$, alkyl containing 1 to 6 carbon atoms, alkoxy containing 1 to 6 carbon atoms or by one or more halogen atoms; or R3, R5 and R6 are independently OR' or OP'; wherein R' is selected from the group consisting of $SO_3$, $SO_2$, $SO_2NHCOH$, $SO_2NHCO$, $SO_2NHCOO$, $SO_2NHCONH$ and $SO_2NHCONH_2$; and R' is optionally substituted by hydrogen or alkyl group optionally substituted by a pyridyl or carbamoyl radical, —$CH_2$-alkenyl containing 3 to 9 carbon atoms, aryl containing 6 to 10 carbon atoms and aralkyl containing 7 to 11 carbon atoms, wherein the nucleus of said aryl or aralkyl is optionally substituted by OH, $NH_2$, $NO_2$, alkyl containing 1 to 6 carbon atoms, alkoxy containing 1 to 6 carbon atoms or by one or more halogen atoms; and P' is selected from the group consisting of $PO(OH)_2$, $PO_3$, $PO_2$, PO, PO(OH)(O—), $PO_2NHCOH$, $PO_2NHCO$, $PO_2NHCOO$, $PO_2NHCONH$ and $PO_2NHCONH_2$; and P' is optionally substituted by hydrogen or alkyl group optionally substituted by a pyridyl or carbamoyl radical, —$CH_2$-alkenyl containing 3 to 9 carbon atoms, aryl containing 6 to 10 carbon atoms and aralkyl containing 7 to 11 carbon atoms, wherein the nucleus of said aryl or aralkyl is optionally substituted by OH, $NH_2$, $NO_2$, alkyl containing 1 to 6 carbon atoms, alkoxy containing 1 to 6 carbon atoms or by one or more halogen atoms.

2. The process of claim 1, wherein R1, R2 and R7 are hydrogen and R3 is $OSO_3H$.

3. The process of claim 1, wherein R1 is piperidinyl, R2 and R7 are hydrogen and R3 is $OSO_3H$.

4. The process of claim 1, wherein R4 is benzyloxy.

5. The process of claim 1, wherein R5 is benzyloxy and R6 and R7 are hydrogen.

6. The process of claim 1, wherein R5 is allyl or trialkylsilyl and R6 is hydrogen.

7. The process of claim 1, comprising treating the compound of Formula (III) with 9-fluorenylmethoxycarbonyl.

8. The process of claim 1, comprising treating the compound of Formula (III) with N,N-carbonyl diimidazole.

9. The process of claim 1, further comprising treating the compound formed after treatment of compound of Formula (III) with a $SO_3$ complex.

10. The process of claim 1, wherein the compound of Formula (I) is trans-7-oxo-6-(sulphooxy)-1,6-diazabicyclo[3,2,1]octane-2-carboxamide or a pharmaceutically acceptable salt thereof.

11. The process of claim 1, wherein the compound of Formula (I) is sodium ({[(2S,5R)-2-carbamoyl-7-oxo-1,6-diazabicyclo[3.2.1]oct-6-yl]oxy}sulphonyl)oxidanide.

12. The process of claim 1, wherein the compound of Formula (II) is benzyl (2S,5R)-5-[(benzyloxy)amino]piperidine-2-carboxylate ethanedioate.

13. The process of claim 1, wherein the compound of Formula (III) is (2S,5R)-5-[(benzyloxy)amino]piperidine-2-carboxamide.

14. The process of claim 13, comprising treating (2S,5R)-5-[(benzyloxy)amino]piperidine-2-carboxamide to prepare (2S,5R)-6-(benzyloxy)-7-oxo-1,6-diazabicyclo[3.2.1 octane-2-carboxamide.

15. ({[(2S,5R)-2-carbamoyl-7-oxo-1,6-diazabicyclo[3.2.1]oct-6-yl]oxy}sulphonyl)oxidanide prepared according to the process of claim 1.

* * * * *